(12) United States Patent
Kim et al.

(10) Patent No.: US 11,692,011 B2
(45) Date of Patent: Jul. 4, 2023

(54) HEPATITIS B VIRUS-DERIVED POLYPEPTIDE AND ANTI-VIRAL USE THEREOF

(71) Applicant: SEOUL NATIONAL UNIVERSITY R&DB FOUNDATION, Seoul (KR)

(72) Inventors: Bum Joon Kim, Seoul (KR); Yu Min Choi, Seoul (KR); Hong Kim, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 7 days.

(21) Appl. No.: 17/090,485

(22) Filed: Nov. 5, 2020

(65) Prior Publication Data

US 2021/0054029 A1    Feb. 25, 2021

Related U.S. Application Data

(63) Continuation-in-part of application No. PCT/KR2019/005302, filed on May 3, 2019.

(30) Foreign Application Priority Data

May 9, 2018 (KR) .................. 10-2018-0053039
May 9, 2018 (KR) .................. 10-2018-0053040

(51) Int. Cl.
| | |
|---|---|
| A61K 38/16 | (2006.01) |
| A61K 38/00 | (2006.01) |
| A61P 31/14 | (2006.01) |
| A61P 31/18 | (2006.01) |
| A61P 31/20 | (2006.01) |
| C07K 14/005 | (2006.01) |
| A61K 31/708 | (2006.01) |

(52) U.S. Cl.
CPC .......... *C07K 14/005* (2013.01); *A61K 31/708* (2013.01); *A61K 38/162* (2013.01); *A61P 31/20* (2018.01); *C12N 2730/10122* (2013.01); *C12N 2730/10133* (2013.01)

(58) Field of Classification Search
CPC .... A61K 31/708; A61K 38/00; A61K 38/162; A61K 38/16; A61P 31/14; A61P 31/18; A61P 31/20; C07K 14/005
See application file for complete search history.

(56) References Cited

U.S. PATENT DOCUMENTS

| | | | | |
|---|---|---|---|---|
| 4,966,848 A | * | 10/1990 | Smith | C12N 9/1029 435/942 |
| 5,223,421 A | * | 6/1993 | Smith | C12N 9/1029 435/255.2 |
| 5,837,218 A | * | 11/1998 | Peers | C07K 14/001 424/1.65 |
| 7,276,483 B1 | * | 10/2007 | Castillo | A61K 38/10 514/17.8 |
| 2003/0171538 A1 | | 9/2003 | Chisari | |

FOREIGN PATENT DOCUMENTS

| | | |
|---|---|---|
| EP | 3 189 850 A1 | 7/2017 |
| KR | 10-2010-0136960 A | 12/2010 |
| KR | 10-2012-0052352 A | 5/2012 |
| KR | 10-2012-0085510 A | 8/2012 |

OTHER PUBLICATIONS

UniProt Accession No. A0A0A9T4M8, pp. 1-2. Integrated into UniProtKb/TrEMBL on Mar. 4, 2015. (Year: 2015).*
UniProt Accession No. A0A0G4NDI1, pp. 1-3. Integrated into UniProtKb/TrEMBL on Sep. 16, 2015. (Year: 2015).*
UniProt Accession No. A0A081CAP7, pp. 1-3. Integrated into UniProtKb/TrEMBL on Oct. 29, 2014. (Year: 2014).*
Kim et al., "HBV polymerase-derived peptide exerts an anti-HIV effect by inhibiting the acetylation of viral integrase," Biochemical and Biophysical Research Communications, May 16, 2018, 501: 541-546. (Year: 2018).*
International Search Report and Written Opinion dated Aug. 14, 2019 in International Application No. PCT/KR2019/005302, in 16 pages. (English translation of ISR.).
Samuel, "Antiviral Actions of Interferons", *Clinical Microbiology Reviews*, vol. 14, No. 4, Oct. 2001, pp. 778-809.

* cited by examiner

*Primary Examiner* — Julie Ha
(74) *Attorney, Agent, or Firm* — Sughrue Mion, PLLC

(57) ABSTRACT

A hepatitis B virus-derived polypeptide exhibits anti-viral effects not only on HIV-1 and HBV but also on all viruses by increasing the expression of type I interferon. The hepatitis B virus-derived polypeptide has a synergistic effect when co-administered with a conventional anti-viral agent. The hepatitis B virus-derived polypeptide is effectively usable in the treatment of virus-related diseases such as AIDS or liver diseases.

19 Claims, 30 Drawing Sheets
Specification includes a Sequence Listing.

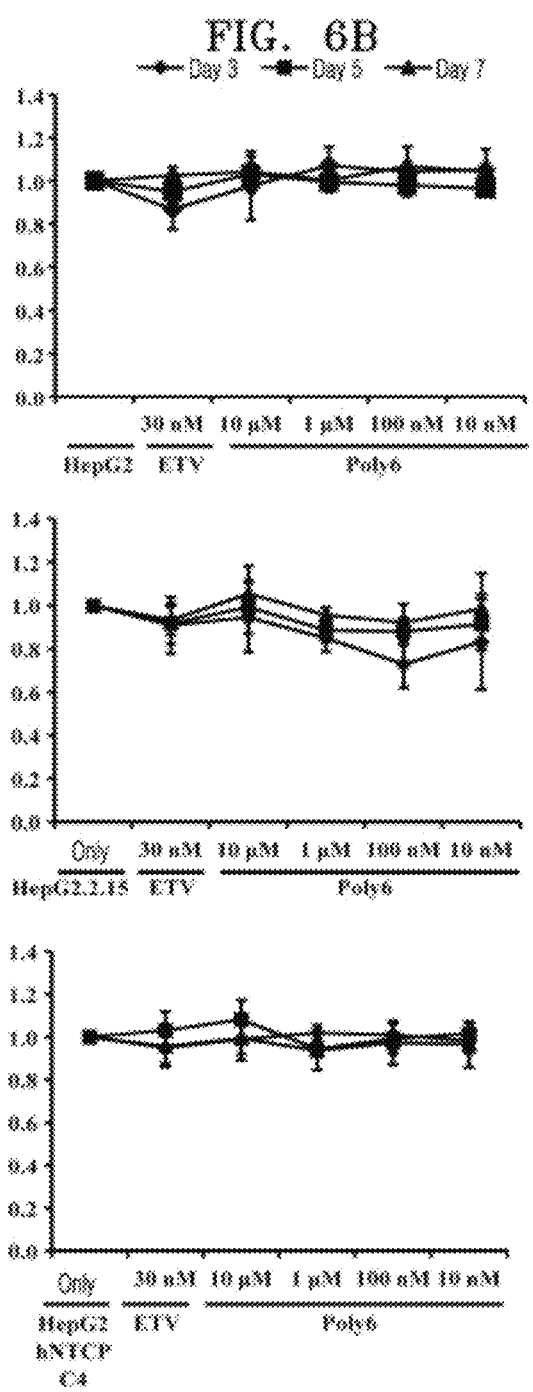

SEQUENCE LISTING

<160> NUMBER OF SEQ ID NOS: 36

<210> SEQ ID NO 1
<211> LENGTH: 5
<212> TYPE: PRT
<213> ORGANISM: Hepatitis B virus

<400> SEQUENCE: 1

Gly Arg Leu Val Phe
1               5

<210> SEQ ID NO 2
<211> LENGTH: 6
<212> TYPE: PRT
<213> ORGANISM: Hepatitis B virus

<400> SEQUENCE: 2

Gly Arg Leu Val Phe Gln

<210> SEQ ID NO 3
<211> LENGTH: 7
<212> TYPE: PRT
<213> ORGANISM: Hepatitis B virus

<400> SEQUENCE: 3

Gly Arg Leu Val Phe Gln Thr
1               5

<210> SEQ ID NO 4
<211> LENGTH: 24
<212> TYPE: DNA
<213> ORGANISM: Artificial Sequence
<220> FEATURE:
<223> OTHER INFORMATION: GagF

<400> SEQUENCE: 4
gcagccatgc aaatgttaaa agag                                          24

<210> SEQ ID NO 5
<211> LENGTH: 22
<212> TYPE: DNA
<213> ORGANISM: Artificial Sequence
<220> FEATURE:
<223> OTHER INFORMATION: GagR

<400> SEQUENCE: 5
tccccttggt tctctcatct gg                                            22

<210> SEQ ID NO 6
<211> LENGTH: 20
<212> TYPE: DNA
<213> ORGANISM: Artificial Sequence
<220> FEATURE:
<223> OTHER INFORMATION: GAPDH-F

<400> SEQUENCE: 6
aatcccatca ccatcttcca                                               20

<210> SEQ ID NO 7
<211> LENGTH: 20
<212> TYPE: DNA
<213> ORGANISM: Artificial Sequence
<220> FEATURE:
<223> OTHER INFORMATION: GAPDH-R

<400> SEQUENCE: 7
tggactccac gacgtactca                                               20

<210> SEQ ID NO 8
<211> LENGTH: 23
<212> TYPE: DNA
<213> ORGANISM: Artificial Sequence
<220> FEATURE:
<223> OTHER INFORMATION: 2-LTR F

<400> SEQUENCE: 8
aactagggaa cccactgctt aag                                           23

<210> SEQ ID NO 9
<211> LENGTH: 24
<212> TYPE: DNA
<213> ORGANISM: Artificial Sequence
<220> FEATURE:

<223> OTHER INFORMATION: 2-LTR R

<400> SEQUENCE: 9
ttcacagatc aaggatatct tgtc                                              24

<210> SEQ ID NO 10
<211> LENGTH: 20
<212> TYPE: DNA
<213> ORGANISM: Artificial Sequence
<220> FEATURE:
<223> OTHER INFORMATION: 2-LTR probe

<400> SEQUENCE: 10
acactacttg aagcactcaa                                                   20

<210> SEQ ID NO 11
<211> LENGTH: 24
<212> TYPE: DNA
<213> ORGANISM: Artificial Sequence
<220> FEATURE:
<223> OTHER INFORMATION: Alu-1F

<400> SEQUENCE: 11
tcccagctac tcgggaggct gagg                                              24

<210> SEQ ID NO 12
<211> LENGTH: 24
<212> TYPE: DNA
<213> ORGANISM: Artificial Sequence
<220> FEATURE:
<223> OTHER INFORMATION: Alu-1R

<400> SEQUENCE: 12
ccctagttag ccagagagct ccca                                              24

<210> SEQ ID NO 13
<211> LENGTH: 20
<212> TYPE: DNA
<213> ORGANISM: Artificial Sequence
<220> FEATURE:
<223> OTHER INFORMATION: Alu-2F

<400> SEQUENCE: 13
acagcctcct agcatttcgt                                                   20

<210> SEQ ID NO 14
<211> LENGTH: 20
<212> TYPE: DNA
<213> ORGANISM: Artificial Sequence
<220> FEATURE:
<223> OTHER INFORMATION: Alu-2R

<400> SEQUENCE: 14
agcggaaagt cccttgtaga                                                   20

<210> SEQ ID NO 15
<211> LENGTH: 20
<212> TYPE: DNA
<213> ORGANISM: Artificial Sequence
<220> FEATURE:
<223> OTHER INFORMATION: Alu probe

<400> SEQUENCE: 15
agcatgggat ggaggacccg                                                   20

```
<210> SEQ ID NO 16
<211> LENGTH: 20
<212> TYPE: DNA
<213> ORGANISM: Artificial Sequence
<220> FEATURE:
<223> OTHER INFORMATION: cccProbe

<400> SEQUENCE: 16
cctaatcatc tcatgttcat                                               20

<210> SEQ ID NO 17
<211> LENGTH: 16
<212> TYPE: DNA
<213> ORGANISM: Artificial Sequence
<220> FEATURE:
<223> OTHER INFORMATION: 3.5-pgProbe

<400> SEQUENCE: 17
ccttggactc ataagg                                                   16

<210> SEQ ID NO 18
<211> LENGTH: 27
<212> TYPE: DNA
<213> ORGANISM: Artificial Sequence
<220> FEATURE:
<223> OTHER INFORMATION: GAPDHprobe

<400> SEQUENCE: 18
cctggccaag gtcatccatg acaactt                                       27

<210> SEQ ID NO 19
<211> LENGTH: 23
<212> TYPE: DNA
<213> ORGANISM: Artificial Sequence
<220> FEATURE:
<223> OTHER INFORMATION: Real-SF

<400> SEQUENCE: 19
ttgacaagaa tcctcacaat acc                                           23

<210> SEQ ID NO 20
<211> LENGTH: 20
<212> TYPE: DNA
<213> ORGANISM: Artificial Sequence
<220> FEATURE:
<223> OTHER INFORMATION: Real-SR

<400> SEQUENCE: 20
ggaggttggg gactgcgaat                                               20

<210> SEQ ID NO 21
<211> LENGTH: 22
<212> TYPE: DNA
<213> ORGANISM: Artificial Sequence
<220> FEATURE:
<223> OTHER INFORMATION: m18S-F

<400> SEQUENCE: 21
cgcggttcta ttttgttggt tt                                            22

<210> SEQ ID NO 22
<211> LENGTH: 19
<212> TYPE: DNA
<213> ORGANISM: Artificial Sequence
<220> FEATURE:
<223> OTHER INFORMATION: m18S-R
```

<400> SEQUENCE: 22
ttcgctctgg tccgtcttg						19

<210> SEQ ID NO 23
<211> LENGTH: 20
<212> TYPE: DNA
<213> ORGANISM: Artificial Sequence
<220> FEATURE:
<223> OTHER INFORMATION: hIFN-beta-F

<400> SEQUENCE: 23
ttgtgcttct ccactacagc						20

<210> SEQ ID NO 24
<211> LENGTH: 20
<212> TYPE: DNA
<213> ORGANISM: Artificial Sequence
<220> FEATURE:
<223> OTHER INFORMATION: hIFN-beta-R

<400> SEQUENCE: 24
ctgtaagtct gttaatgaag						20

<210> SEQ ID NO 25
<211> LENGTH: 19
<212> TYPE: DNA
<213> ORGANISM: Artificial Sequence
<220> FEATURE:
<223> OTHER INFORMATION: hIFN-alpha-F

<400> SEQUENCE: 25
gactccatct tggctgtga						19

<210> SEQ ID NO 26
<211> LENGTH: 21
<212> TYPE: DNA
<213> ORGANISM: Artificial Sequence
<220> FEATURE:
<223> OTHER INFORMATION: hIFN-alpha-R

<400> SEQUENCE: 26
tgatttctgc tctgacaacc t						21

<210> SEQ ID NO 27
<211> LENGTH: 19
<212> TYPE: DNA
<213> ORGANISM: Artificial Sequence
<220> FEATURE:
<223> OTHER INFORMATION: hISG15-F

<400> SEQUENCE: 27
agctccatgt cggtgtcag						19

<210> SEQ ID NO 28
<211> LENGTH: 20
<212> TYPE: DNA
<213> ORGANISM: Artificial Sequence
<220> FEATURE:
<223> OTHER INFORMATION: hISG15-R

<400> SEQUENCE: 28
gaaggtcagc cagaacaggt						20

<210> SEQ ID NO 29
<211> LENGTH: 21

```
<212> TYPE: DNA
<213> ORGANISM: Artificial Sequence
<220> FEATURE:
<223> OTHER INFORMATION: hRIG-I-F

<400> SEQUENCE: 29
ggacgtggca aaacaaatca g                                              21

<210> SEQ ID NO 30
<211> LENGTH: 21
<212> TYPE: DNA
<213> ORGANISM: Artificial Sequence
<220> FEATURE:
<223> OTHER INFORMATION: hRIG-I-R

<400> SEQUENCE: 30
gcaatgtcaa tgccttcatc a                                              21

<210> SEQ ID NO 31
<211> LENGTH: 20
<212> TYPE: DNA
<213> ORGANISM: Artificial Sequence
<220> FEATURE:
<223> OTHER INFORMATION: hTNF-alpha-F

<400> SEQUENCE: 31
ggagaagggt gaccgactca                                                20

<210> SEQ ID NO 32
<211> LENGTH: 17
<212> TYPE: DNA
<213> ORGANISM: Artificial Sequence
<220> FEATURE:
<223> OTHER INFORMATION: hTNF-alpha-R

<400> SEQUENCE: 32
ctgcccagac tcggcaa                                                   17

<210> SEQ ID NO 33
<211> LENGTH: 20
<212> TYPE: DNA
<213> ORGANISM: Artificial Sequence
<220> FEATURE:
<223> OTHER INFORMATION: mIFN-beta-F

<400> SEQUENCE: 33
cacagccctc tccatcaact                                                20

<210> SEQ ID NO 34
<211> LENGTH: 20
<212> TYPE: DNA
<213> ORGANISM: Artificial Sequence
<220> FEATURE:
<223> OTHER INFORMATION: mIFN-beta-R

<400> SEQUENCE: 34
tcccacgtca atctttcctc                                                20

<210> SEQ ID NO 35
<211> LENGTH: 22
<212> TYPE: DNA
<213> ORGANISM: Artificial Sequence
<220> FEATURE:
<223> OTHER INFORMATION: m18S-F

<400> SEQUENCE: 35
```

```
cgcggttcta ttttgttggt tt                                              22

<210> SEQ ID NO 36
<211> LENGTH: 19
<212> TYPE: DNA
<213> ORGANISM: Artificial Sequence
<220> FEATURE:
<223> OTHER INFORMATION: m18S-R

<400> SEQUENCE: 36
ttcgctctgg tccgtcttg                                                  19
```

HEPATITIS B VIRUS-DERIVED POLYPEPTIDE AND ANTI-VIRAL USE THEREOF

CROSS REFERENCE TO RELATED APPLICATIONS

This is a continuation-in-part application of International Patent Application No. PCT/KR2019/005302, filed on May 3, 2019, which claims priority to Korean patent application Nos. 10-2018-0053039 and 10-2018-0053040 both filed on May 9, 2018, contents of all of which are incorporated herein by reference in their entireties.

REFERENCE TO ELECTRONIC SEQUENCE LISTING

The present application is being filed along with an Electronic Sequence Listing. The Electronic Sequence Listing is provided as a file entitled WVIP005001P1SEQLIST.txt, created on Oct. 26, 2020 and last modified on Nov. 5, 2020, which is 7,182 bytes in size. The information in the electronic format of the Electronic Sequence Listing is incorporated herein by reference in its entirety.

BACKGROUND

Technical Field

The present disclosure relates to a hepatitis B virus-derived polypeptide and anti-viral use thereof.

Description of Related Technology

Human immunodeficiency virus (HIV), which causes acquired immune deficiency syndrome (AIDS), has infected 38 million people as of 2015, and thus HIV is a source of infection that needs attention worldwide. Despite the introduction of highly active antiretroviral therapy (HAART), it is still difficult to eradicate the virus.

Traditional drugs have targeted viral enzymes such as reverse transcriptase (RT), protease, integrase (IN), etc. Raltegravir (ISENTRESS/MK-0518) is a prototypical integrase strand transfer inhibitor (INSTI) approved for clinical use due to strong viral load reduction. However, resistance to raltegravir has been revealed in clinical trials as well as in optimized HAART methods.

On the other hand, approximately 240 million to approximately 350 million people worldwide are infected with hepatitis B virus (HBV), and they show various clinical courses of asymptomatic infection, chronic hepatitis, cirrhosis, and transition to hepatocellular carcinoma. Infections with HBV, which accounts for 53% of all causes of hepatocellular carcinoma, is especially high in Asia. In most countries in Asia, HBV carrier rates amount to 5% to 35%. There are host factors, viral factors, and environmental factors related to clinical symptoms caused by HBV infection.

SUMMARY

An aspect provides a polypeptide consisting of any one amino acid sequence selected from the group consisting of SEQ ID NO: 1, SEQ ID NO: 2, and SEQ ID NO: 3.

Another aspect provides an anti-viral pharmaceutical composition including the polypeptide.

Still another aspect provides a pharmaceutical composition for preventing or treating acquired immune deficiency syndrome (AIDS), the pharmaceutical composition including the polypeptide.

Still another aspect provides a pharmaceutical composition for preventing or treating a liver disease, the pharmaceutical composition including the polypeptide.

Still another aspect provides an anti-viral health functional food including the polypeptide.

Still another aspect provides a method of preventing or treating viral infection and symptoms related thereto, the method including administering the pharmaceutical composition to an individual.

An aspect provides a polypeptide consisting of any one amino acid sequence selected from the group consisting of SEQ ID NO: 1, SEQ ID NO: 2, and SEQ ID NO: 3.

The term "polypeptide" means a polymer consisting of two or more amino acids linked by amide bonds (or peptide bonds). The polypeptide may consist of any one amino acid sequence selected from the group consisting of SEQ ID NO: 1, SEQ ID NO: 2, and SEQ ID NO: 3, and specifically, the amino acid sequence of SEQ ID NO: 2. The polypeptide may include a polypeptide having about 70% or more, about 75% or more, about 80% or more, about 85% or more, about 90% or more, about 92% or more, about 95% or more, about 97% or more, about 98% or more, or about 99% or more sequence homology to the amino acid sequence of SEQ ID NO: 1, SEQ ID NO: 2, or SEQ ID NO: 3.

Further, a protecting group may be attached to the N- or C-terminus of the polypeptide to obtain better chemical stability, enhanced pharmacological properties (half-life, absorption, potency, efficacy, etc.), altered specificity (e.g., a broad-spectrum of biological activities), or reduced antigenicity. The protecting group may be an acetyl group, a fluorenyl methoxycarbonyl group, a formyl group, a palmitoyl group, a myristyl group, a stearyl group, or polyethylene glycol (PEG), but may include any component without limitation, as long as it is able to improve modification of the polypeptide, particularly, stability of the polypeptide.

The term "stability" refers to storage stability (e.g., room-temperature storage stability) as well as in-vivo stability that protects the peptide of the present disclosure from attack of protease in vivo.

Furthermore, the polypeptide may additionally include an amino acid sequence which is prepared for the specific purpose of a targeting sequence, a tag, or a labeled residue.

The term "homology" is to indicate a similar degree to a wide-type amino acid sequence, and comparison of the homology may be performed using a comparison program which is widely known in the art, and homology between two or more sequences may be calculated as a percentage (%).

The polypeptide may be derived from a natural source, or may be obtained by various polypeptide synthesis methods widely known in the art. For example, the polypeptide may be prepared by polynucleotide recombination and protein expression systems, or by in-vitro synthesis through chemical synthesis such as peptide synthesis, and by cell-free protein synthesis. For example, the polypeptide may be a peptide, an extract of plant-derived tissues or cells, a product obtained by culturing microorganisms (e.g., bacteria or fungi, particularly, yeasts), and specifically, the polypeptide may be derived from hepatitis B virus (HBV) polymerase, and more specifically, derived from the preS1 region of the HBV polymerase.

The polypeptide may be "end-capping modified polypeptide" or "protected polypeptide". Since the present peptides are preferably utilized in therapeutics which requires the peptides to be in soluble form, the peptides of some embodiments of the invention preferably include one or more non-natural or natural polar amino acids, including but not limited to serine and threonine which are capable of increasing peptide solubility due to their hydroxyl-containing side chain. The N and C termini of the peptides of the present invention may be protected by functional groups. Suitable functional groups are described in Green and Wuts, "Protecting Groups in Organic Synthesis", John Wiley and Sons, Chapters 5 and 7, 1991, the teachings of which are incorporated herein by reference. Thus, the polypeptide may be modified at the N-(amine) terminus and/or the C-(carboxyl) terminus thereof so as to produce an end capping modified peptide.

As used herein, the phrases "end-capping modified polypeptide" and "protected polypeptide", which are interchangeably used herein, refer to a polypeptide which has been modified at the N-(amine) terminus and/or the C-(carboxyl) terminus thereof. The end-capping modification refers to the attachment of a chemical moiety to the terminus of the polypeptide, so as to form a cap. Such a chemical moiety is referred to herein as an end capping moiety and is typically also referred to herein and in the art, interchangeably, as a peptide protecting moiety or group. Hydroxyl protecting groups include but are not limited to esters, carbonates and carbamate protecting groups. Amine protecting groups include but are not limited to alkoxy and aryloxy carbonyl groups. Carboxylic acid protecting groups include but are not limited to aliphatic, benzylic and aryl esters.

The phrase "end-capping moiety", as used herein, refers to a moiety that when attached to the terminus of the peptide, modifies the N and/or C terminal ends(s) of the peptide. The end-capping modification typically results in masking the charge of the peptide terminus, and/or altering chemical features thereof, such as, hydrophobicity, hydrophilicity, reactivity, solubility and the like. By selecting the nature of the end capping modification, the hydrophobicity/hydrophilicity, as well as the solubility of the peptide can be finely controlled. According to specific embodiments, the protecting groups facilitate transport of the peptide attached thereto into a cell. These moieties can be cleaved in vivo, either by hydrolysis or enzymatically, inside the cell.

According to specific embodiments, the end-capping modification does not compromise the biological activity (i.e. anti-viral activity) of the polypeptide. Examples of moieties suitable for peptide end-capping modification can be found, for example, in Green et al., "Protective Groups in Organic Chemistry", (Wiley, 2.sup.nd ed. 1991) and Harrison et al., "Compendium of Synthetic Organic Methods", Vols. 1-8 (John Wiley and Sons, 1971-1996). According to specific embodiments, the end-capping comprises an N terminus end-capping. Examples of N-terminus end-capping moieties include, but are not limited to, formyl, acetyl (also denoted herein as "Ac"), trifluoroacetyl, benzyl, benzyloxycarbonyl (also denoted herein as "Cbz"), tert-butoxycarbonyl (also denote d herein as "Boc"), trimethylsilyl (also denoted "TMS"), 2-trimethylsilyl-ethanesulfonyl (also denoted "SES"), trityl and substituted trityl groups, allyloxycarbonyl, 9-fluorenylmethyloxycarbonyl (also denoted herein as "Fmoc"), and nitro-veratryloxycarbonyl ("NVOC").

According to specific embodiments, the N terminus end-capping comprises an Acetyl.

According to specific embodiments, the end-capping comprises a C terminus end-capping.

Examples of C-terminus end-capping moieties are typically moieties that lead to acylation of the carboxy group at the C-terminus and include, but are not limited to, benzyl and trityl ethers as well as alkyl ethers, tetrahydropyranyl ethers, trialkylsilyl ethers, allyl ethers, monomethoxytrityl and dimethoxytrityl. Alternatively the —COOH group of the C-terminus end-capping may be modified to an amide group.

The polypeptide may have anti-viral activity. For example, the virus may be at least one selected from the group consisting of adenovirus, smallpox virus, polio virus, measles virus, severe fever with thrombocytopenia syndrome virus, influenza virus, hepatitis C virus, human immunodeficiency virus-1 (HIV-1), and hepatitis B virus (HBV), and specifically, at least one selected from the group consisting of HIV-1 and HBV.

Another aspect provides an anti-viral pharmaceutical composition including the polypeptide.

With regard to the pharmaceutical composition, the "polypeptide", etc. is the same as described above.

Further, the composition may further include an anti-viral agent.

The anti-viral agent may be, for example, at least one selected from the group consisting of acyclovir, famciclovir, valacyclovir, ganciclovir, amprenavir, abacavir, ansamycin, cidofovir, darunavir, delavirdine, efavirenz, etravirine, famciclovir, hypericin, indinavir, lamivudine, lobucavir, nelfinavir, nevirapine, novaferon, ritonavir, saquinavir, stavudine, tipranavir, virazole, ribavirin, zalcitabine, zidovudine, maraviroc, raltegravir, elvitegravir, didanosine, tenofovir, emtricitabine, lopinavir, atazanavir, enfuvirtide, clevudine, entecavir, adefovir, oseltamivir, zanamivir, peramivir, amantadine, and telbivudine, specifically, at least one selected from the group consisting of clevudine, entecavir, and adefovir, and more specifically, entecavir.

The composition may further include the anti-viral agent to remarkably increase the anti-viral effect, thereby exhibiting a synergistic effect. For example, when the anti-viral agent is entecavir, an anti-HBV effect and an effect on type I interferon expression may be remarkably increased by a synergistic effect.

Further, the virus may be at least one selected from the group consisting of adenovirus, smallpox virus, polio virus, measles virus, severe fever with thrombocytopenia syndrome virus, influenza virus, hepatitis C virus, human immunodeficiency virus-1 (HIV-1), and hepatitis B virus (HBV), and specifically, at least one selected from the group consisting of HIV-1 and HBV.

The polypeptide may suppress replication of virus. Specifically, the polypeptide may inhibit the acetylation of HIV-1 integrase to inhibit its activity, leading to suppression of HIV-1 replication. Further, the polypeptide may increase mitochondrial reactive oxygen species in cells, and may increase expression of IFN-α and IFN-β which are type I interferons, thereby inhibiting synthesis of HBcAg or nucleocapsid of HBV. As a result, HBV replication may be suppressed.

Without limitation to a particular theory, IFN-induced proteins implicated in the antiviral actions of IFNs are RNA-dependent protein kinase (PKR), 2', 5'-oligoadenylate synthetase (OAS), and RNase L and Mx protein GTPase. Double-stranded RNA modulates protein phosphorylation and RNA degradation catalyzed by IFN-induced PKR kinase and 2'-5'-oligo-adenylate dependent RNase L, respectively, and also plays a role in RNA editing by IFN-induced RNA specific adenosine deaminase (ADAR1). IFN also induces inducible nitric oxide synthase (iNOS2) and major histocompatibility complex (MHC) I and II proteins, all of which play roles in immune responses to infections (see Clin Microbiol Rev. 2001 October; 14(4): 778-809). The above document is hereby incorporated by reference in its entirety.

Therefore, the polypeptide according to one specific embodiment may increase IFN expression to exhibit antiviral activity against all viruses.

The term "prevention" means all of the actions by which an individual's disease caused by virus is restrained or retarded by the administration of the pharmaceutical composition according to an aspect.

The term "treatment" means all of the actions by which symptoms of an individual's disease caused by virus have taken a turn for the better or been modified favorably by the administration of the pharmaceutical composition according to an aspect.

According to an aspect, the polypeptide inhibits acetylation of HIV-1 integrase, thereby suppressing HIV-1 replication. A therapeutic effect on AIDS may be achieved by suppressing HIV-1 replication.

According to an aspect, the polypeptide may increase mitochondrial stress to increase intracellular reactive oxygen species, and to increase type I interferon expression, thereby inhibiting nucleocapsid synthesis. As a result, HBV replication may be suppressed, thereby exhibiting a therapeutic effect on liver diseases.

The pharmaceutical composition may include the active ingredient alone or may be provided as a pharmaceutical composition including one or more pharmaceutically acceptable carriers, excipients, or diluents.

Specifically, the carrier may be, for example, a colloidal suspension, a powder, a saline, lipids, liposomes, microsphere, or nanospheric particles. These may form a complex with a carrier or may be associated with the carrier, and may be delivered in vivo using a delivery system which is known in the art, such as lipids, liposomes, microparticles, gold, nanoparticles, polymers, condensation reagents, polysaccharides, polyamino acids, dendrimers, saponins, adsorption enhancers, or fatty acids.

The pharmaceutical composition may include a pharmaceutically acceptable carrier, i.e., lactose, dextrose, sucrose, sorbitol, mannitol, starch, acacia, rubber, calcium phosphate, alginate, gelatin, calcium silicate, microcrystalline cellulose, polyvinylpyrrolidone, cellulose, water, syrup, methylcellulose, methyl hydroxybenzoate, propyl hydroxybenzoate, talc, magnesium stearate, mineral oil, etc., which is generally used in formulation.

Further, when the pharmaceutical composition is formulated, it may be prepared using diluents or excipients such as lubricants, sweeteners, flavoring agents, emulsifiers, suspensions, preservatives, fillers, extenders, binders, wetting agents, disintegrants, surfactants, etc., which are commonly used. Solid preparations for oral administration may include tablets, pills, powders, granules, capsules, etc. Such a solid formulation may be prepared by mixing the composition with at least one excipient, for example, starch, calcium carbonate, sucrose, lactose, gelatin, etc. In addition to the simple excipients, lubricants such as magnesium stearate or talc may be used. Liquid preparations for oral administration may include suspension, solutions for internal use, emulsions, syrups, etc. In addition to water and liquid paraffin, which are commonly used simple diluents, various excipients, for example, wetting agents, sweeteners, fragrances, preservatives, etc. may be included. Preparations for parental administration may include sterile aqueous solutions, non-aqueous solvents, suspensions, emulsions, lyophilized preparations, and suppositories. For the non-aqueous solvents and the suspensions, propylene glycol, polyethylene glycol, vegetable oil such as olive oil, injectable ester such as ethyl oleate, etc. may be used. As bases of the suppositories, Witepsol, macrogol, Tween 61, cacao fat, laurin fat, glycerogelatin, etc. may be used. When prepared in the form of eye drops, a known diluent, excipient, etc. may be used.

The term "pharmaceutically acceptable" refers to a non-toxic property to cells or humans exposed to the composition.

In addition, the pharmaceutical composition may be provided by mixing with a known anti-viral composition. In other words, the pharmaceutical composition may be administered in combination with a known composition having anti-cataract, anti-viral effects.

The term "administration" refers to introduction of a given substance into an individual in an appropriate manner.

The term "individual" refers to a subject in need of treatment of a disease caused by virus, and more specifically, mammals such as human or non-human primates, mice, dogs, cats, horses, cattle, etc.

The pharmaceutical composition may be administered orally or parenterally (e.g., intramuscularly, intravenously, intraperitoneally, intradermally, subcutaneously, or topically) according to a desired method, and an administration dosage may be appropriately selected by those skilled in the art, depending on a patient's condition and body weight, a degree of a disease, the type of a drug, administration route and time.

The pharmaceutical composition may be administered in a pharmaceutically effective amount. The term "pharmaceutically effective amount" refers to an amount sufficient to treat a diseases, at a reasonable benefit/risk ratio applicable to any medical treatment. An effective dose level may be determined depending on factors including the type and severity of a patient's disease, drug activity, drug sensitivity, administration time, administration route, excretion rate, treatment period, and drugs concurrently used, and other factors well known in the medical field. Specifically, the pharmaceutical composition may be administered in an amount of 0.01 mg/kg/day to 1000 mg/kg/day, and more specifically, 0.1 mg/kg/day to 500 mg/kg/day. The administration may be performed once or divided into several times per day.

The pharmaceutical composition according to an aspect may be used singly or in combination with other anti-inflammatory agents. The pharmaceutical composition may be administered together with a known anti-inflammatory agents simultaneously, separately, or sequentially in single or multiple administration. It is important to administer an amount to obtain the maximum effect with a minimum amount without adverse effects considering the factors described above, and the amount may be readily determined by one of ordinary skill in the art.

Specifically, the effective amount of the pharmaceutical composition may vary depending on a patient's age, sex, health conditions, body weight, absorption rate of active ingredients in vivo, an inactivation rate and excretion rate, the kind of a disease, and drug(s) administered in combination, and may be increased or decreased depending on the administration route, severity of obesity, sex, body weight, age, etc.

Still another aspect provides a pharmaceutical composition for preventing or treating acquired immune deficiency syndrome (AIDS), the pharmaceutical composition including the polypeptide.

The AIDS may be caused by HIV-1 infection.

Still another aspect provides a pharmaceutical composition for preventing or treating a liver disease, the pharmaceutical composition including the polypeptide.

The liver disease may be caused by HBV infection, specifically, may be at least one selected from the group consisting of hepatitis, cirrhosis, and liver cancer, and more specifically, may be developed from hepatitis B.

Still another aspect provides an anti-viral health functional food including the polypeptide.

With regard to the health functional food, the "polypeptide", "AIDS" and "liver diseases", "virus", etc. may be the same as described above.

As used herein, the term "improvement" refers to all of the actions by which parameters associated with the conditions under treatment, for example, the symptoms, are at least lessened. In this regard, the health functional food may be used for preventing or improving AIDS or liver diseases simultaneously in combination with or separately from a pharmaceutical drug for treatment, before or after occurrence of the corresponding disease.

In the health functional food, the active ingredient may be added as it is into the food, may be used along with other foods or food ingredients, and may be appropriately used according to a common method. The mixed amount of the active ingredient may be appropriately determined according to the intended use (for prevention or improvement). Generally, in the preparation of foods or beverages, the health functional food may be added specifically in an amount of 15 wt % or less, and more specifically in an amount of 10 wt % or less with respect to raw materials. However, in the case of a long-term intake for health and hygiene or for health control, the amount may be less than the above range.

The health functional food may be prepared into one formulation selected from the group consisting of tablets, pills, powders, granules, powders, capsules, and liquid formulations by further including one or more of diluents, excipients, or additives such as carriers, fillers, extenders, binders, wetting agents, disintegrants, surfactants, etc. The foods that may be added include various foods, powders, granules, tablets, capsules, syrups, beverages, gums, teas, vitamin complexes, health functional foods, etc.

Specific examples of the carrier, excipient, diluent, and additive may be at least one selected from the group consisting of lactose, dextrose, sucrose, sorbitol, mannitol, erythritol, starch, acacia rubber, calcium phosphate, alginate, gelatin, calcium phosphate, calcium silicate, microcrystalline cellulose, polyvinylpyrrolidone, cellulose, polyvinylpyrrolidone, methylcellulose, water, sugar syrup, methylcellulose, methylhydroxy benzoate, propylhydroxy benzoate, talc, magnesium stearate, and mineral oil.

The health functional food may include other ingredients as necessary ingredients without particular limitations, in addition to the active ingredient. For example, the health functional food may include various kinds of flavoring agents, natural carbohydrates, etc. as additional ingredients, as in common beverages. Examples of the above-described natural carbohydrates may include common saccharides such as monosaccharides, e.g., glucose, fructose, etc.; disaccharides, e.g., maltose, sucrose, etc.; and polysaccharides, e.g., dextrin, cyclodextrin, etc.; and sugar alcohols such as xylitol, sorbitol, erythritol, etc. As flavoring agents other than those described above, natural flavoring agents (taumatin, *Stevia* extracts (e.g., rebaudioside A, glycyrrhizin, etc.)) and synthetic flavoring agents (saccharin, aspartame, etc.) may be advantageously used. A proportion of the natural carbohydrates may be appropriately determined by one of ordinary skill in the art.

Additionally, the health functional food according to an aspect may include a variety of nutrients, vitamins, minerals (electrolytes), flavoring agents such as synthetic and/or natural flavoring agents, colorants and fillers (cheese, chocolate, etc.), pectic acid and salts thereof, alginic acid and salts thereof, organic acids, protective colloidal thickening agents, pH modifiers, stabilizers, preservatives, glycerin, alcohols, carbonating agents used in carbonated beverages, etc. These ingredients may be used independently or in combination. A proportion of these additives may also be appropriately selected by one of ordinary skill in the art.

Still another aspect provides a method of preventing or treating viral infection and symptoms related thereto, the method including administering the pharmaceutical composition to an individual.

The "polypeptide", "individual", "administration", "pharmaceutical composition", "virus", etc. are the same as described above.

A polypeptide according to an aspect may increase type I interferon expression to exhibit anti-HIV-1 and anti-HBV effects as well as to exhibit antiviral effects against all viruses, and the polypeptide also has a synergistic effect when administered in combination with an existing antiviral agent. Accordingly, the polypeptide may be usefully applied to treatment of virus-related diseases such as AIDS, liver diseases, etc.

BRIEF DESCRIPTION OF DRAWINGS

FIGS. 6A and 6B show polypeptide candidates, Poly5, Poly6, and Poly7, and a comparison of anti-viral effects of individual materials, and a cell viability assay by candidate treatment, wherein FIG. 6A shows a comparison of s/e antigen-reducing effects of a hepatitis B virus-derived polypeptide (Poly6) according to an aspect and candidate polypeptides (Poly5, Poly7), and FIG. 6B shows results of the cell viability assay of the polypeptide according to an aspect.

FIGS. 7A, 7B, 7C, 7D, and 7E show HBV replication suppression by a polypeptide according to an aspect at a chronic infection stage, and anti-HBV effects by the polypeptide according to an aspect in HBV-susceptible cells, wherein FIG. 7A shows HBsAg levels, FIG. 7B shows HBeAg levels, FIG. 7C shows viral titers, FIG. 7D shows Southern blot results, and FIG. 7E shows a relationship ($IC_{50}$) between the administration dosage of the polypeptide according to one aspect and HBV replication.

FIGS. 9A and 9B shows HBV inhibitory effects of a polypeptide according to an aspect on mouse models, wherein FIG. 9A shows HBsAg levels according to treatment with PBS, Lamivudine (3TC), and the polypeptide according to an aspect, and FIG. 9B shows HBV DNA levels according to treatment with PBS, Lamivudine (3TC), and the polypeptide according to an aspect.

FIGS. 10A, 10B, and 10C show a test of mitochondrial oxidative stress production by a polypeptide according to an aspect, wherein FIG. 10A shows mitochondrial reactive oxygen species (mtROS) levels (rotenone is a positive control for mitochondrial oxidative stress) over time according to treatment with each material, FIG. 10B shows mtROS levels according to concentrations of the polypeptide according to an aspect, and FIG. 10C shows mtROS levels according to treatment with the polypeptide according to an aspect and treatment with an oxidative stress inhibitor (MitoTempo).

FIGS. 11A and 11B show increased patterns of type I interferon (Type 1 IFN) by a polypeptide according to an aspect, wherein FIG. 11A shows mRNA levels of IFN-β, RIG-I, and ISG15 according to treatment with the polypeptide, FIG. 11B shows luciferase expression levels in a cell supernatant of hMH55-293-ISRE cells treated with each material.

FIGS. 12A and 12B show blocking of an anti-HBV effect of poly6 through neutralization of an IFN-1 receptor, wherein FIG. 12A shows that e-antigen and extracellular HBV DNA levels that were reduced by an aspect of treatment were recovered by treatment with neutralizing antibodies, and FIG. 12B shows that IFN-I mRNA levels that were increased by an aspect of treatment were reduced.

FIGS. 13A, 13B, and 13C show a synergistic antiviral effect by combination treatment with a polypeptide according to an aspect and entecavir (ETV), wherein FIG. 13A shows the synergistic effects on extracellular HBV DNA reduction according to the combination treatment, FIG. 13B shows a cytotoxicity test according to the combination treatment, and FIG. 13C shows reduction in levels of s and e antigens according to the combination treatment.

FIGS. 14A and 14B show a synergistic effect on IFN-I increase according to combination treatment with entecavir (ETV) and a polypeptide according to an aspect, wherein FIG. 14A shows IFN-α, IFN-β, and TNF-α mRNA levels according to the combination treatment and FIG. 14B shows luciferase expression levels in a cell supernatant of hMH55-293-ISRE cells according to the combination treatment.

DETAILED DESCRIPTION

Current available therapeutic agents for chronic hepatitis include interferons, which are immunomodulators, lamivudine, which is a nucleoside analogue, etc. Among them, interferon-α, the efficacy of which has been recognized in the last decade, has the disadvantages of being expensive, having side effects, and being less effective in Asian patients who have problems with infection immediately after birth. Other therapeutic agents, nucleoside analogues, have the advantage of being orally administered. However, since nucleoside analogues act on DNA polymerase and inhibit viral replication, there are problems in that they do not act directly on non-replicative viruses, making it difficult to completely remove HBV from the body, and resistance develops, etc.

In view of this technical background, there is a need to develop new therapeutic agents that are able to alleviate AIDS or liver diseases through anti-HIV-1 and anti-HBV effects.

Hereinafter, the present disclosure will be described in more detail with reference to exemplary embodiments. However, these exemplary embodiments are only for illustrating the present disclosure, and the scope of the present disclosure is not limited to these exemplary embodiments.

EXAMPLE

Example 1. Examination of Anti-HIV-1 Efficacy

Reference Example Statistical Analysis

Statistical comparisons between control and experimental groups were analyzed using one-way ANOVA. The p value of statistical significance was set as follows: $p<0.05$ (*), 0.01 (), or 0.001 (*). All experiments were independently repeated three times.

Figure 1A:
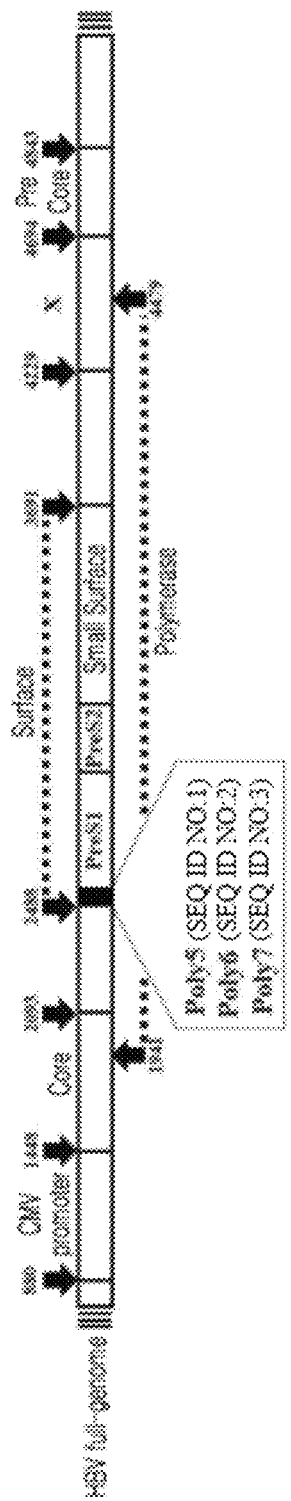
FIG. 1A shows an illustration of positions of hepatitis B virus-derived polypeptides (Poly5, Poly6, and Poly7) according to an aspect.

Experimental Example 1. Identification of HBV Polymerase-Derived Peptide Having Anti-HIV-1 Effects In this Experimental Example, it was examined whether an HBV polymerase-derived peptide has anti-HIV-1 effects. In detail, since deletion of 15, 18, and 21 nucleotides at the preS1 start in hepatitis B virus of chronic patients with genotype C2 infection may contribute disease progression by regulating viral replication, three kinds of candidate peptides were selected from polymerase regions corresponding to deletion of 15, 18, and 21 nucleotides in this Experimental Example. These peptides were called Poly5 (GRLVF, SEQ ID NO: 1), Poly6 (GRLVFQ, SEQ ID NO: 2), or Poly7 (GRLVFQT, SEQ ID NO: 3) (FIG. 1A), and each peptide was synthesized by 9-fluorenylmethoxycarbonyl (Fmoc)-based solid phase synthesis in Peptron Inc., and all peptides used in Examples had purity of 95% or more, as measured by high performance liquid chromatography. To evaluate anti-HIV-1 effects of the three polypeptides, cell-based anti-viral effects were analyzed. MT-4 cells ($4 \times 10^5$ cells) were infected with HIV-1 ($4 \times 10^5$ $CCID_{50}$) for 1 hour. The MT-4 cells were obtained from NIH/AIDS Research and Reference Reagent Program. 293FT cells were transfected for 48 hr with HIV-1 using a pBR_HIV-1_M_NL4-3_IRES_eGFP vector (DS441) which co-expresses Nef and enhanced green fluorescence protein (eGFP) from a single bicistronic RNA, and Lipofectamine 2000 reagent (Life Technologies). A supernatant containing a viral precursor HIV-1 was harvested, and the viral titer was determined using p24 ELISA (ABL). For amplification of infectious HIV-1, MT-4 cells were infected with the viral precursor HIV-1 at a multiplicity of infection (MOI) of 0.5 for 72 hr. After centrifugation and filtration of the collected supernatant, p24 ELISA was used for titration of infectious virus, and stored at −70° C. until use.

After washing cells with PBS, infected cells were treated with dimethyl sulfoxide (DMSO), azidothymidine (AZT; 3-azido-3-deoxythymidine), and Poly5 to Poly7. In this regard, DMSO and AZT were purchased from Sigma-Aldrich. After 2 days of incubation, GFP images were obtained using a fluorescence microscope. The relative GFP intensity was determined using an ImageJ software program (National Institutes of Health) in pixels per area. The supernatant and cells were collected and subjected to RNA extraction, and then RT-qPCR was performed to determine viral titers. To measure virus in the supernatant, p24 ELISA was used. Cell viability against the treated reagents was assessed by an MTT assay.

To examine the role of HSP90 (cell signaling) in the antiviral effects of Poly5 to Poly7, MT-4 cells were infected with HIV-1 for 1 hr, and then treated with an HSP90 antibody (1 µg/ml) or 17-AAG (Calbiochem, 1 µM) for 1 hr to block HSP90 activity. Cells were treated with DMSO, AZT, or Poly6 and incubated for 48 hr. HIV-LTR-dependent synthesis of GFP was confirmed by Western blotting using a GFP antibody (Santa Cruz Biotechnology).

Figure 1B:
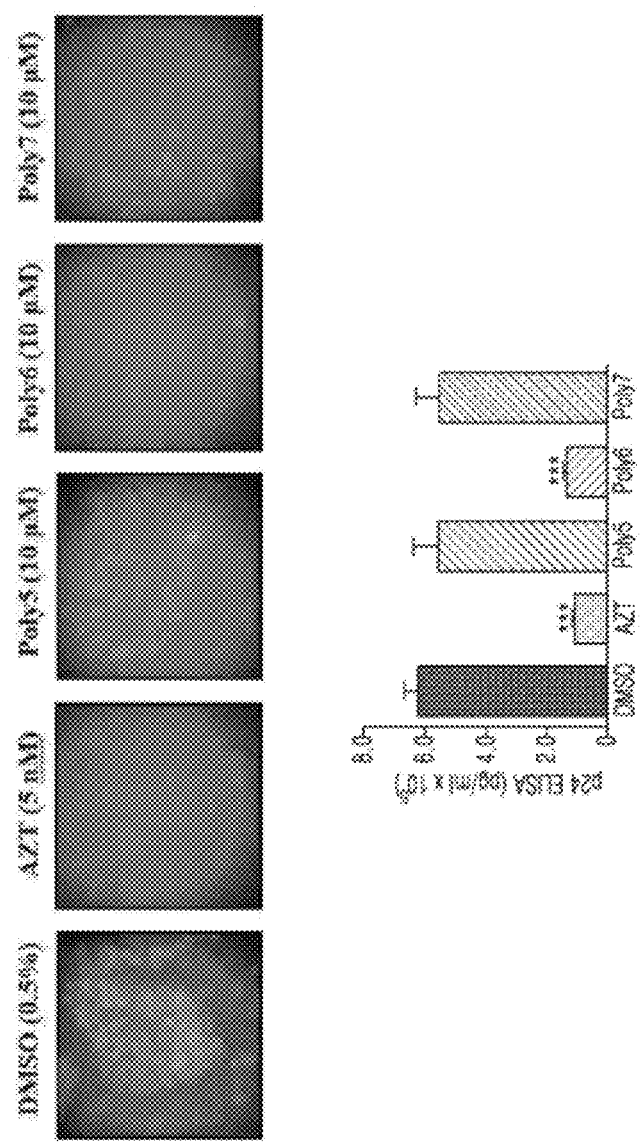
FIG. 1B shows results of analyzing anti-HIV1 effects.

HIV-1-infected MT-4 cells were treated with DMSO (0.5%), AZT (5 nM), or each 10 µM of three kinds of candidates, and 2 days later, GFP imaging and p24 ELISA were performed to examine HIV-1 titers. As a result, it was confirmed that virus production was reduced by Poly5 and Poly7, and in particular, considerably reduced by Poly6 (FIG. 1B).

Experimental Example 2. Cytotoxicity Assay

Figure 2A:
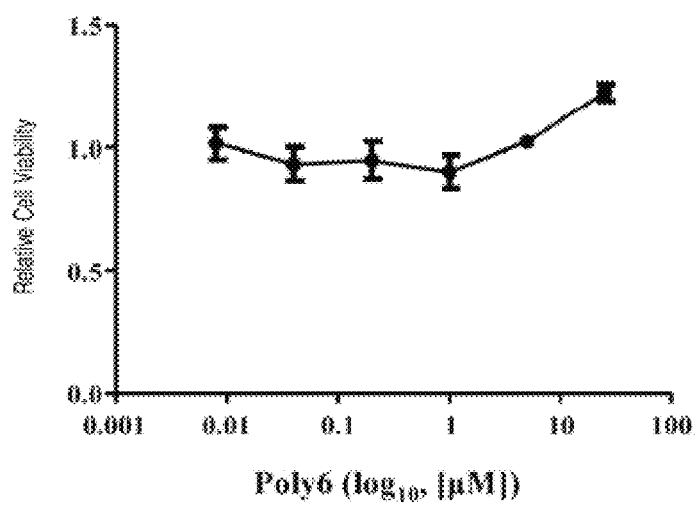
FIG. 2A shows a cytotoxicity test of a polypeptide according to an aspect.
Figure 2B:
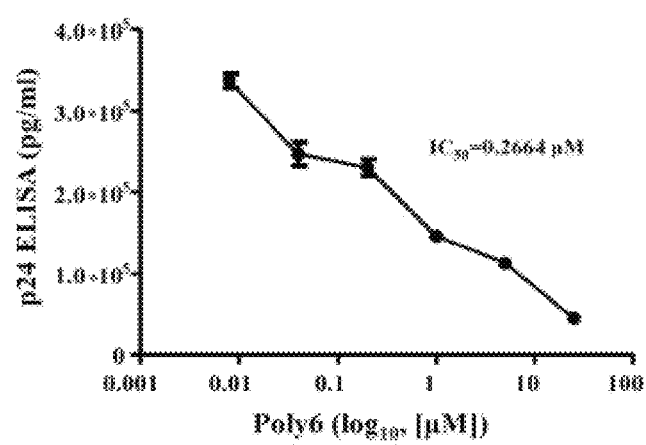
FIG. 2B shows a test of anti-HIV-1 activity of the polypeptide according to an aspect.
Figure 2C:
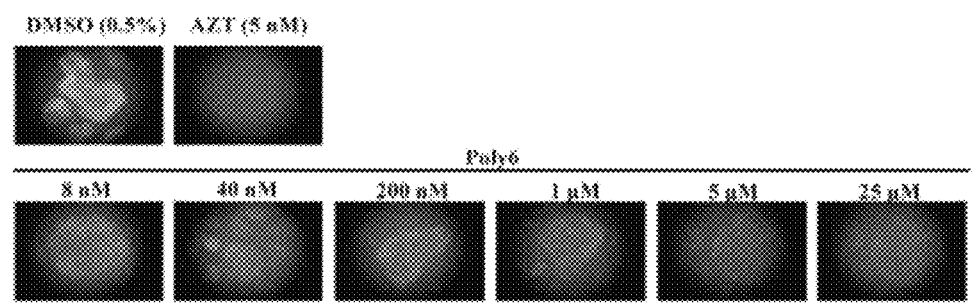
FIG. 2C shows a test of HIV-1 GFP expression-inhibition by the polypeptide according to an aspect.
Figure 2D:
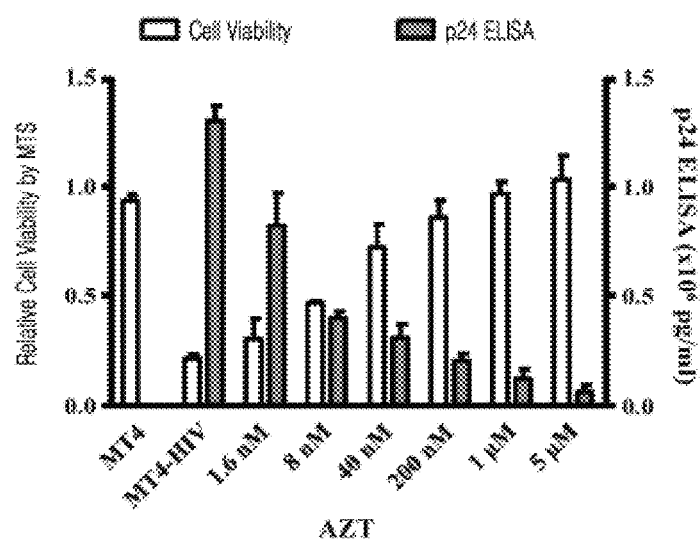
FIGS. 2D and 2E show tests of cell degeneration-inhibitory effects of AZT and the polypeptide according to an aspect.
Figure 2E:
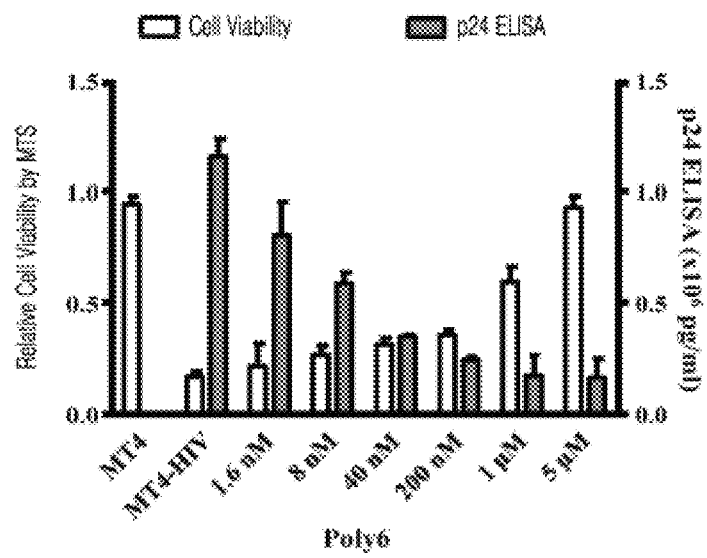

In this Experimental Example, prior to examination of the effect of Poly6, cytotoxic effects of Poly6 was analyzed to exclude the possibility that Poly6 affects HIV-1 replication due to its nonspecific cytotoxicity. In detail, MT-4 cells were prepared at a density of $1 \times 10^4$ cells, and incubated with varying concentrations of Poly6 for 5 days. Cytotoxicity was determined using an MTT assay kit (Promega). To analyze the anti-cytotoxic effect of Poly6 from cell death caused by cytotoxicity due to HIV-infection, MT-4 cells ($1 \times 10^4$ cells) were infected with HIV-1 ($1 \times 10^4$ $CCID_{50}$), incubated for five days, and then subjected to cell viability assays. In addition, to determine HIV-1 titers in the supernatant, p24 ELISA was performed. As a result, Poly6 did not exert significant cytotoxic activity against MT-4 cells up to 25 µM for 5 days (FIG. 2A). To produce HIV-1 from 293FT cells, the cells were transfected with pBR_HIV-1_M_NL4-3_IRES_eGFP vector, and anti-HIV-1 activity of Poly6 in MT-4 cells were determined by p24 ELISA. HIV-1 replication was inhibited by Poly6 in a dose-dependent manner, and the mean 50% inhibitory concentration ($IC_{50}$) value was about 0.2664 µM (FIG. 2B). Additionally, GFP expression, which depends on the activation of HIV-1 LTR, was also diminished by Poly6 in a dose-dependent manner (FIG. 2C). In HIV-1-infected MT-4 cells, cell death signaling pathway is activated due to virus replication, leading to cell destruction. Therefore, it was confirmed that, after treatment with AZT, cell protective effect was ultimately shown in MT-4 cells due to anti-viral effect of AZT. Similar to AZT, cytopathic inhibitory effects of Poly6 on HIV-1-infected MT-4 cells were analyzed. As a result, as shown in FIG. 2, AZT (FIG. 2D)) and Poly6 (FIG. 2E)) showed a significant cell protective effect in a dose-dependent manner. 5 µM of Poly6 was sufficient to confer almost 100% cell protection from HIV-1-mediated cell death. As the cell protective ability by the anti-HIV-1 effect of Poly6 increased, viral p24 levels in the cell supernatant were relatively decreased by suppressing HIV-1 (FIG. 2E). Taken together, these experimental results suggest, in Experimental Example, that Poly6 plays a pivotal role in protecting MT-4 cell viability by suppressing HIV-1 replication and inhibiting cell degeneration.

Experimental Example 3. Examination of HIV-1 Replication-Inhibitory Effect in Human Peripheral Blood Mononuclear Cells (PBMCs)

In this Experimental Example, the anti-HIV-1 effect of Poly6 was examined in Ex-vivo. In detail, PBMCs were infected with HIV-1. Human PBMCs were separated using Biocoll (BIOCHROME), and PBMCs were incubated in an RPMI1640 medium supplemented with 10% FBS and 1 µg/ml phytohemaggulutinin (PHA; Sigma-Aldrich), and IL-2 (100 U/ml; PEPROTECH) for 3 days. PHA-stimulated PBMC cells were infected with HIV-1 at a multiplicity of infection (MOI) of 0.1, and treated with reagents, followed by incubation for 5 days. To determine the viral titers in PBMCs, viral RNAs were isolated from cells, and analyzed by RT-qPCR as described. GFP expression was observed using a fluorescence microscope, and Western blot analysis was performed using a GFP antibody.

At this time, to determine HIV-1 viral titers, p24 ELISA (ABL, Rockville, Md.) was conducted according to the manufacturer's protocol. HIV-1 RNAs from cell culture supernatants and cells were purified using a QIAamp UltraSens Virus kit (QIAGEN), and quantitated by RT-qPCR using primers specific to Gag region of HIV-1. Glyceraldehyde phosphate dehydrogenase (GAPDH) was used as a reference gene for normalization. Primers such as GagF, GCAGCCATGCAAATGTTAAAAGAG (forward, SEQ ID NO: 4) and GagR, TCCCCTTGGTTCTCTCATCTGG (reverse, SEQ ID NO: 5) and GAPDH-F, AATCCCATCAC-CATCTTCCA (forward, SEQ ID NO: 6), and GAPDH-R, TGGACTCCACGACGTACTCA (reverse, SEQ ID NO: 7) were used in RTqPCR. An HIV-1 Genesig Standard kit (Primer design) was used to calibrate the viral titers.

Figure 3A:
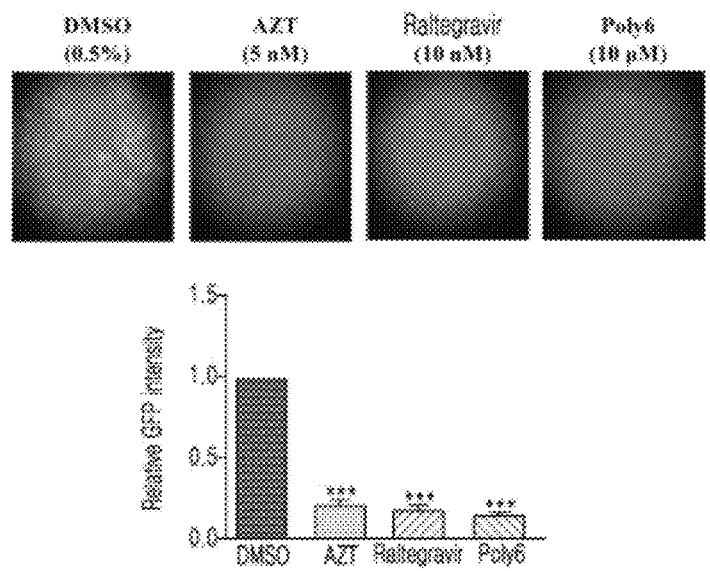
FIG. 3A shows a test of HIV-1 GFP expression inhibition by a polypeptide according to an aspect and other anti-HIV-1 agents.
Figure 3B:
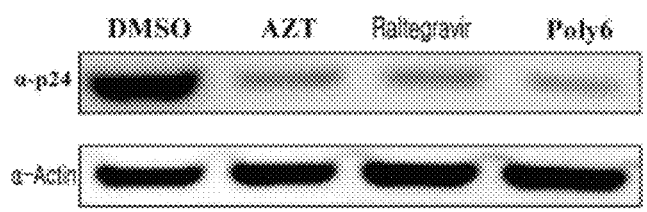
FIG. 3B shows a test of p24 expression inhibition by the polypeptide according to an aspect and other anti-HIV-1 agents.
Figure 3C:
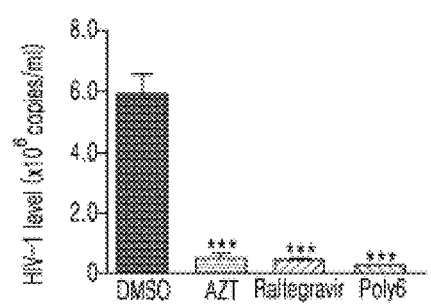
FIG. 3C shows a test of HIV-1 level inhibition by the polypeptide according to an aspect and other anti-HIV-1 agents.

PBMC cells were infected with HIV-1, and then incubated in the presence of DMSO (0.5%), AZT (5 nM), Raltegravir (10 nM), or Poly6 (10 µM) for 5 days. It was confirmed that, as compared with DMSO, GFP and p24 protein expression in PBMC cells was significantly reduced by Poly6 in the similar level to those in AZT or Raltegravir (FIGS. 3A and 3B). It was also confirmed that, as compared with DMSO, HIV-1 replication in PBMC cells was significantly reduced by Poly6 in the similar level to those in AZT or Raltegravir (FIG. 3C). These results suggest that Poly6 is able to suppress HIV-1 replication in human PBMC cells as well as in MT-4 cells.

Experimental Example 4. Examination of HIV-1 Integration-Inhibitory Effect

In this Experimental Example, to analyze integration of HIV-1 DNA into the host genome, 2-long terminal repeat (2-LTR) and Alu PCR were performed. In detail, 2-LTR PCR was used to detect circular viral DNA that was left unintegrated in the cell cytoplasm, and Alu PCR was performed to amplify the integrated viral DNA. Reagents were treated for 48 hr, and then viral DNA was extracted from HIV-1-infected MT-4 cells using a QIAamp MinElute Virus Spin Kit (QIAGEN). As primers and probes for 2-LTR PCR analysis, 2-LTR F (MH535), AACTAGGGAACC-CACTGCTTAAG (forward, SEQ ID NO: 8), 2-LTR R (MH536), TTCACAGATCAAGGATATCTTGTC (reverse, SEQ ID NO: 9) and FAM-ACACTACTTGAAGCACT-CAA-TAMRA (SEQ ID NO: 10) as a 2-LTR probe were used, and Alu-1F, TCCCAGCTACTCGGGAGGCTGAGG (forward, SEQ ID NO: 11) and Alu-1R, CCCTAGT-TAGCCAGAGAGCTCCCA (reverse, SEQ ID NO: 12) and secondary Alu PCR forward primer, Alu-2F, ACAGCCTCCTAGCATTTCGT (forward, SEQ ID NO: 13), Alu-2R, AGCGGAAAGTCCCTTGTAGA (reverse, SEQ ID NO: 14) and FAM-AGCATGGGATG-GAGGACCCG-TAMRA (SEQ ID NO: 15) as an Alu PCR probe were used.

In this Experimental Example, to reveal a mechanism of integration inhibition by Poly6, Western blot and immuno-precipitation assay were performed using integrase and a p300 antibody (Santa Cruz Biotechnology). For immuno-precipitation assay, MT-4 cells were infected with HIV-1 for 1 hr, and then treated with DMSO (0.5%), AZT (5 nM), Raltegravir (10 nM), or Poly6 (10 µM) for 48 hr. Cells were lysed by treatment with RIPA (Abcam) buffer, and then the whole lysate was washed in advance with 10 µl of Protein A/G PLUS-Agarose (sc2003, Santa Cruz) and the supernatant was collected. The supernatant was incubated with 20 µg of the antibody for 1 hr at 4° C., and then 10 µl of Protein A/G PLUS-Agarose was added thereto, followed by incubation overnight at 4° C. while rotating at 360°. After the final wash, immunoprecipitates were collected and the resulting precipitates were loaded for Western blot analysis.

Figure 4A:
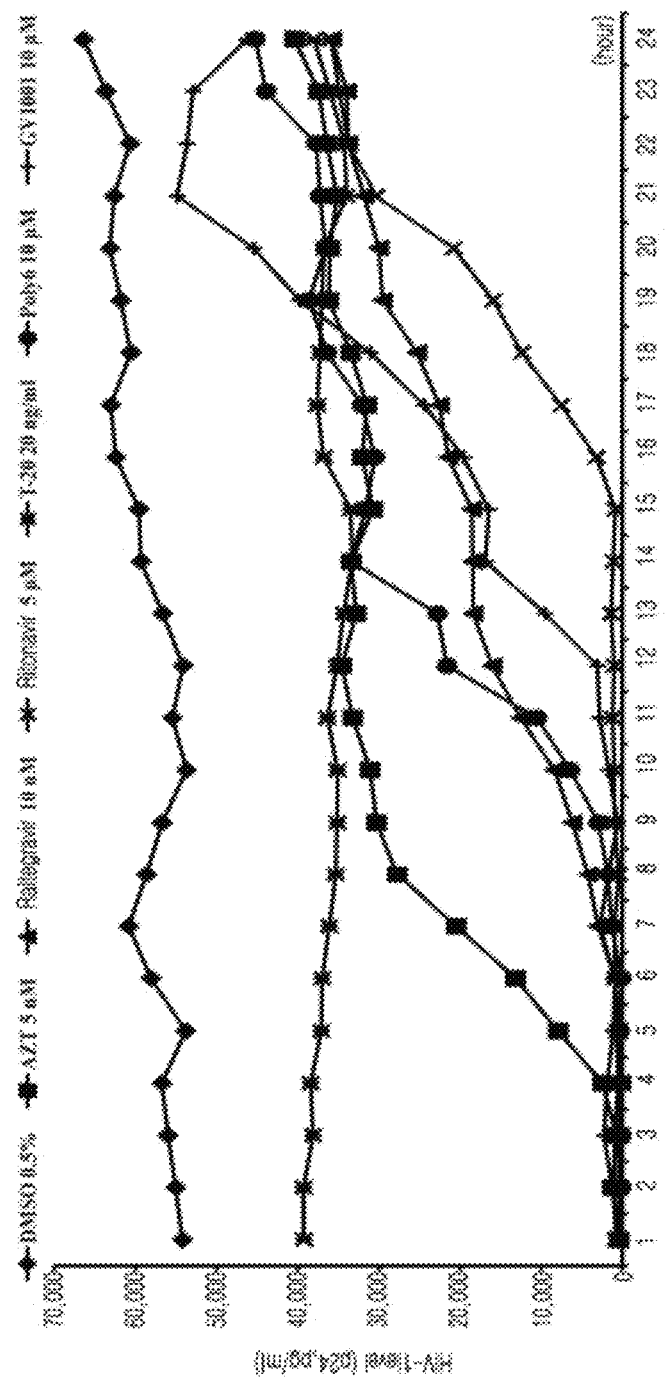
FIGS. 4A and 4B show a test of HIV-1 level inhibition over time by a polypeptide according to an aspect and other anti-HIV-1 agents.
Figure 4B:
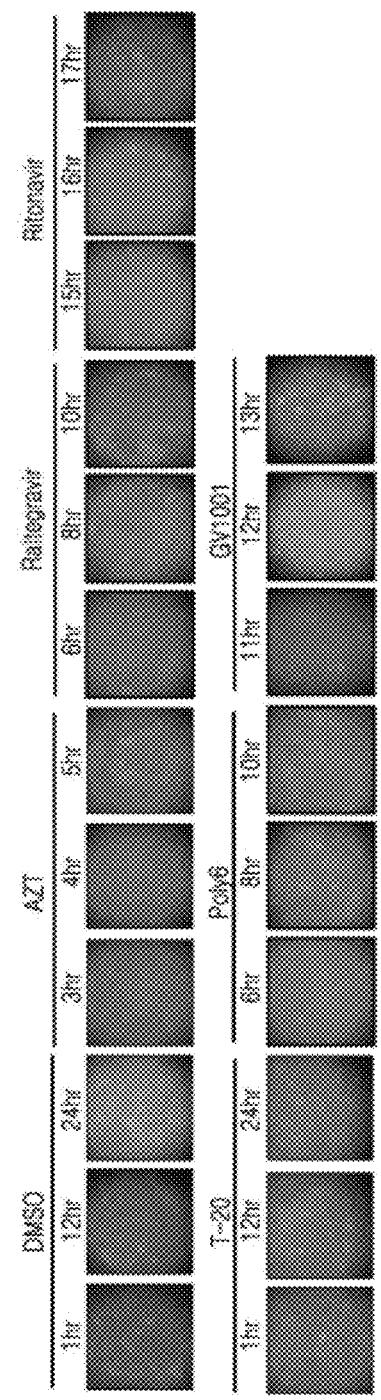

Meanwhile, when MT-4 cells are infected with HIV-1, HIV-1 replication proceeds through several stages. Newly developed anti-HIV-1 reagents have several mechanisms of action, because there are several stages in the HIV-1 life cycle, such as viral attachment, integration, transcription, or viral synthesis. Accordingly, to further delineate the underlying mechanism of HIV-1 inhibition by Poly6, a time-of-addition (TOA) study was performed using Poly6 and several anti-HIV-1 drugs capable of suppressing different stages of the HIV-1 life cycle in MT-4 cells, such as AZT (reverse transcriptase inhibition), raltegravir (integrase inhibition), ritonavir, T20 (inhibition of virus emergence), etc. At this time, T-20, raltegravir and ritonavir were obtained through the NIH/AIDS Research and Reference Reagent Program (NIH). TOA assay showed that the inhibition of HIV-1 replication by each reagent was well represented to a time point corresponding to the replication step targeted by the drugs, and Poly6 started to lose drug efficacy at the time point between 6 hr and 8 hr (FIG. 4A). As shown in the TOA results of raltegravir which is an integrase inhibitor having the similar mechanism of inhibition, intracellular GFP analysis also supports the TOA results (FIG. 4B). Taken together, these results support that Poly6 exhibits the anti-HIV-1 effect by suppressing activity of viral integrase.

Experimental Example 5. Detailed Examination of Mechanism of HIV-1 Inhibition by Poly6

Figure 5A:
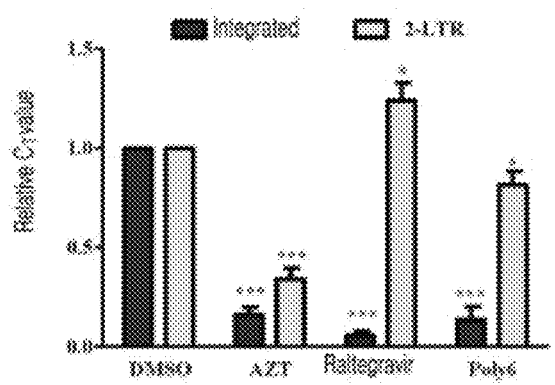
FIG. 5A shows comparative data of a 2-LTR circle and integrated cDNA amounts by a polypeptide according to an aspect and other anti-HIV-1 agents.
Figure 5B:
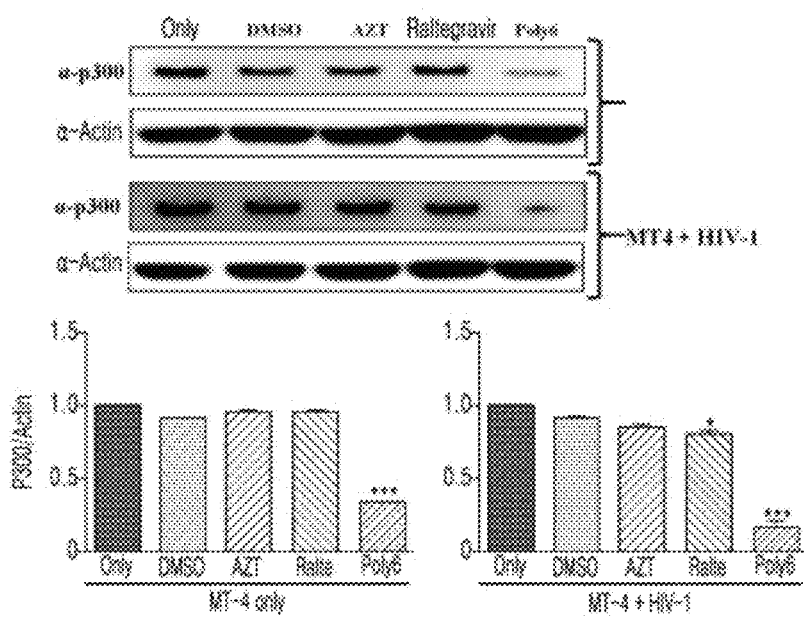
FIG. 5B shows comparative data of p300 expression by the polypeptide according to an aspect and other anti-HIV-1 agents.
Figure 5C:
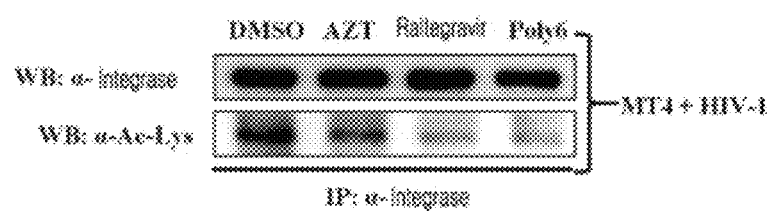
FIG. 5C shows comparative data of integrase acetylation by the polypeptide according to an aspect and other anti-HIV-1 agents.

This Experimental Example was performed to demonstrate TOA data regarding HIV-1 integrase inhibition by Poly6. In detail, integrase circle formation was detected in HIV-1-infected MT-4 cells using Alu PCR and 2-LTR PCR. It is known that when HIV-1 cDNA enters the nuclei of cells, but integration does not occur, HIV-1 cDNA itself replicates to form 2-LTR circle. Unlike Raltegravir which is an integrase inhibitor, the level of 2-LTR circle was increased by Poly6, and the number of integrated cDNA was remarkably reduced in HIV-1-infected MT-4 cells (FIG. 5A). This result indicates that Poly6 suppresses HIV-1 replication by blocking the integration process of integrase. Acetylation of integrase by an intracellular factor such as p300 during the intracellular integration of virus is already known. To examine a fundamental mechanism of the integration-inhibitory activity by Poly6 action, it was first investigated by immunoblotting how Poly6 affects p300 protein expression in non-infected MT-4 cells and HIV-1-infected MT-4 cells. As a result, it was found that Poly6 more efficiently reduced p300 expression in non-infected MT-4 cells, as compared with DMSO, AZT, or Raltegravir (FIG. 5B). Next, to examine whether the reduced p300 causes inhibitory effect on acetylation of virus integrase after immunoprecipitation by integrase, antibodies were applied to infected MT-4 cells treated with DMSO, AZT, Raltegravir, or Poly6. Subsequently, immunoblotting was performed using an antibody specific to acetylated lysine (cell signaling). As a result, it was confirmed that Poly6 and Raltegravir inhibit acetylation of integrase (FIG. 5C).

Taken together, these results indicate that HIV-1 activity inhibition of Poly6 occurs by inhibiting acetylation of integrase by p300.

Example 2. Examination of Anti-HBV Efficacy

Experimental Example 1. Identification of HBV Polymerase-Derived Peptides Having Anti-HBV Effects and Analysis of Cell Viability In this Experimental Example, HBV polymerase-derived peptides having anti-HBV effects were identified, and cell viability upon treatment thereof was analyzed. To evaluate anti-viral effects of the above-described three candidate peptides, Poly5 (GRLVF, SEQ ID NO: 1), Poly6 (GRLVFQ, SEQ ID NO: 2), or Poly7 (GRLVFQT, SEQ ID NO: 3, FIG. 1A), HepG2.2.15 (a human-derived hepatocellular carcinoma cell HepG2 with permanent integration of HBV) or HepG2 cells transiently transfected with pHBV-1.2x-Wild-type (WT) (Genotype C) were treated with PBS (0.5%), entecavir (ETV, Sigma-Aldrich, 30 nM) or three kinds of candidates (10 µM) for 2 days using Lipofectamine 2000 reagent (Life Technologies) according to the manufacturer's protocol. Then, quantitative PCR and ELISA were performed to examine virion replication and HBV surface antigen (HBsAg). At this time, respective peptides were synthesized by solid-phase synthesis in Peptron Inc., and the peptides had purity of 95% or more, as measured by high performance liquid chromatography. Further, oligonucleotides for quantitative real-time PCR and probe for TaqMan probe hybridization PCR are shown in Table 1 below.

TABLE 1

TaqMan Probe

| Name | Sequences (5'-FAM to TAMRA-3') | Position | SEQ ID NO. |
|---|---|---|---|
| ccc Probe | CCT AAT CAT CTC ATG TTC AT | 1834-1853 | 16 |

TABLE 1-continued

| | TaqMan Probe | | |
|---|---|---|---|
| Name | Sequences (5'-FAM to TAMRA-3') | Position | SEQ ID NO. |
| 3.5-pg Probe | CCT TGG ACT CAT AAG G | 2457-2472 | 17 |
| GAPDH probe | CCT GGC CAA GGT CAT CCA TGA CAA CTT | | 18 |

Figure 6A:
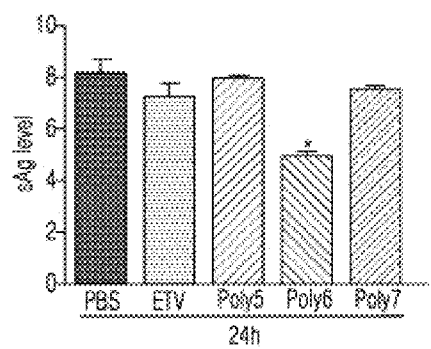
Figure 6A:
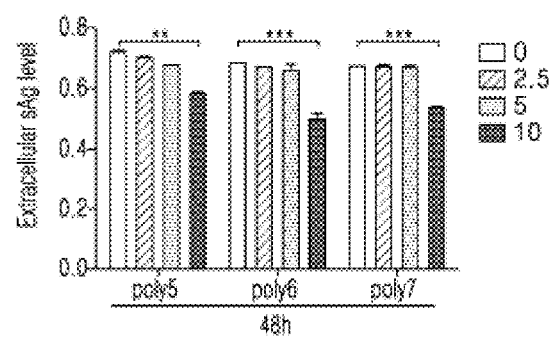
Figure 6A:
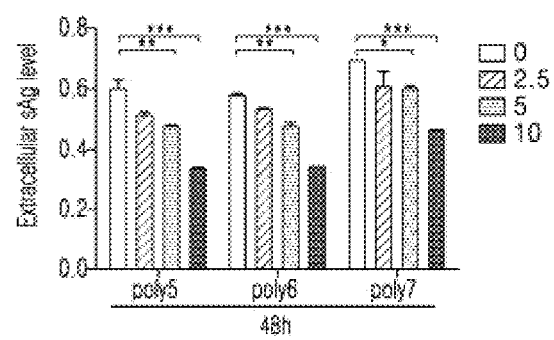

As a result, s antigen and e antigen were reduced in all of the groups treated with Poly5, Poly6 or Poly7 for 48 hr, and the most prominent antigen-reducing effect was observed in the Poly6-treated group, as comparing various concentrations. When treated for 24 hr, significant envelope antigen-reducing effect was observed only in the Poly6-treated group, as compared with ETV (FIG. 6A). Therefore, in this experiment, Poly6 peptide derived from a polymerase region overlapped by 18-nucleotide (nt) deletion of preS1 was selected, and its anti-HBV effect was examined.

In this Experimental Example, prior to examination of anti-viral effect of Poly6, cell viability by Poly6 was observed to examine the possibility that Poly6 affects HBV replication due to its non-specific cytotoxicity.

In detail, HepG2, HepG2.2.15, and HepG2-hNTCP-C4 cells (expressing NTCP receptors on the cell membrane) were plated in a 96 microplate ($1 \times 10^4$ cells/well), and incubated for 5 days with increasing concentrations of ETV (30 nM) and Poly6. For an MTS assay, a cell-titer 96 aqueous one solution was directly added to each well, and the plate was incubated for 3 hr. The plate was read at 490 nm, and each analysis was repeated in triplicate. At this time, for HBV infection analysis, HepG2.2.15 cell supernatant containing 2% DMSO was collected every three days for 15 days, and virions were precipitated with 6% PEG8000 on ice for 1 hr, and concentrated using a ultra-centrifuge at 4° C. and 100,000 g for 3 hr The pellets were re-suspended in 1×PBS containing 10% FBS, and then stored at −80° C. until use. Cells were seeded in a 6-well plate, and infected at $8 \times 10^4$ GEq/cell in the presence of 4% PEG8000 overnight. Next day, the cells were washed with PBS three times, and treated with PBS (0.5%), ETV (30 nM), or Poly6 (10 μM) for 5 days until analysis.

As a result, Poly6 did not exert significant cytotoxic activity against HepG2, HepG2.2.15, and HepG2-hNTCP-C4 cells up to 10 μM as time passed, and did not affect cell viability (FIG. 6B).

Experimental Example 2. Examination of Anti-Viral Efficacy of Poly6 in In-Vitro System Chronic HBV infection is known to cause severe liver diseases such as cirrhosis and hepatocellular carcinoma, unlike acute infection. Therefore, it is important to develop anti-HBV drugs that overcome chronic infections. However, since the HBV genome is integrated into the host chromosome, the complete removal of the virus from human liver and serum remains a difficult problem. Therefore, in this Experimental Example, to evaluate the anti-viral effect of Poly6, HepG2.2.15 permanent cell line that continuously expresses HBV was treated with Poly6. Further, HepG2 cells were seeded in a 6-well plate, and then transiently transfected with pHBV-1.2x-WT. HepG2 cells having pHBV-1.2x-WT or HepG2-2.15 cells were treated with PBS (0.5%), ETV (30 nM), or Poly6 (10 μM) for 24 hr or 48 hr, and then supernatants and pellets were used to perform various analyses. To measure secreted HBsAg and HBeAg in culture supernatants, HBsAg (BIOKIT) and HBeAg (AccuDiag) ELISA were performed according to experimental methods provided. For detection of 8-hydroxy-2'-deoxyguanosine (8-OHdG) activity, an 8-OHdG assay kit (OxiSelect Oxidative DNA Damage ELISA kit, Cell Biolabs) and ELISA were performed according to the manufacturer's protocol.

Figure 7A:
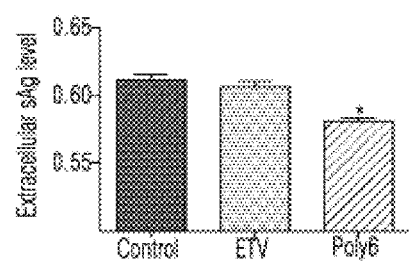
Figure 7B:
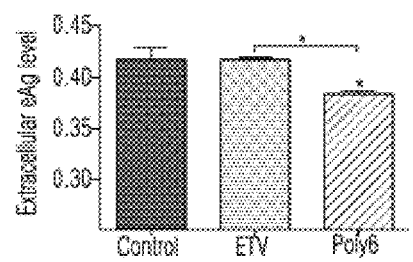
Figure 7C:
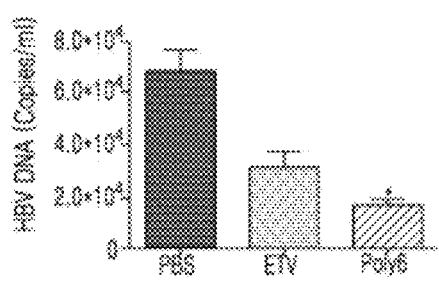
Figure 8A:
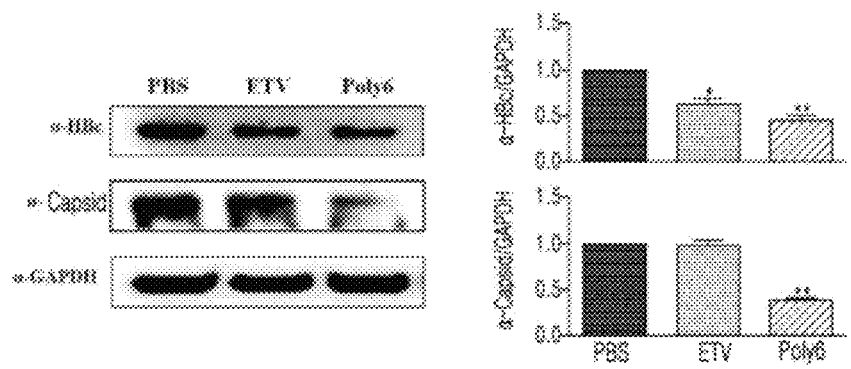
FIG. 8A shows results of examining core protein and capsid formation after treatment with PBS, ETV, and the polypeptide according to one aspect.
Figure 8B:
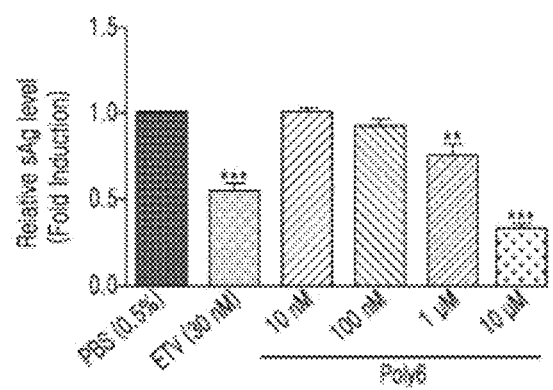
FIG. 8B shows results of measuring HBsAg after infecting HepG2-hNTCP-C4 with each material and an HBV virion.
Figure 8C:
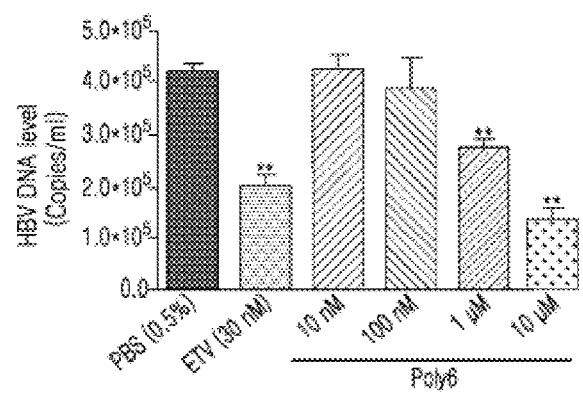
FIG. 8C shows results of measuring viral DNA to examine anti-HBV effects in infection models according to dosages of the polypeptide according to an aspect.

As a result, after treatment with PBS, ETV, and Poly6 for 2 days, a statistically significant reduction in extracellular HBsAg and HBeAg levels was observed in the Poly6-treated group, and viral replication levels were more remarkably reduced by Poly6. Viral replication was also reduced by ETV, but there was no statistical significance between ETV and PBS (FIGS. 7A to 7C) (FIGS. 8B and 8C).

To measure extracellular virion secretion, Southern blot analysis was performed. In detail, before ultra-centrifugation at 4° C. and 24,000 rpm for 3 hr, cell debris was removed, and virions were precipitated from the supernatant using 8% PEG6000 (Sigma) on ice for 1 hr. Pellets were harvested with PBS, and HBV DNA was collected using a QIAamp DNA mini kit (QIAGEN) according to the manufacturers instructions. Viral DNA was measured using quantitative real-time PCR (Q-PCR). PCR amplification was performed using a QPCR primer set targeting a small surface gene, which is designed to amplify an a101-bp product (Table 2). Q-PCR was performed using a commercial SensiFAST SYBR Lo-ROX kit (BIOLINE) and an HBV Genesig standard kit (Primer design) to calibrate a viral load. In addition, to detect extracellular HBV DNA, supernatants were collected and HBV particles were precipitated using 6% PEG8000 (Sigma) as described above. Virus pellets were collected from PBS and DNA was extracted with a lysis buffer (0.25% SDS, 250 mM Tris-HCl, pH 7.4 and 250 mM EDTA). Purified HBV DNA was separated on a 1% agarose gel, transferred to a nylon membrane (Hybond N+; Amersham) by Southern blotting, and hybridized with a 32P-labeled wild-type, full length HBV DNA probe. Analysis was performed using a random primer DNA labeling kit (TaKaRa). Autoradiography was performed and analyzed using a BAS 2500 image analyzer (Fuji Photo Film).

TABLE 2

| | Primer | | |
|---|---|---|---|
| Name | Sequences (5' to 3') | Position | SEQ ID NO. |
| Real-SF | TTG ACA AGA ATC CTC ACA ATA CC | 218-240 | 19 |
| Real-SR | GGA GGT TGG GGA CTG CGA AT | 309-328 | 20 |
| m18S-F | CGC GGT TCT ATT TTG GTT T | | 21 |
| m18S-R | TTC GCT CTG GTC CGT CTT G | | 22 |
| hIFN-β-F | TTG TGC TTC TCC ACT ACA GC | | 23 |
| hIFN-β-R | CTG TAA GTC TGT TAA TGA AG | | 24 |
| hIFN-α-F | GAC TCC ATC TTG GCT GTG A | | 25 |
| hIFN-α-R | TGA TTT CTG CTC TGA CAA CCT | | 26 |
| hISG15-F | AGC TCC ATG TCG GTG TCA G | | 27 |
| hISG15-R | GAA GGT CAG CCA GAA CAG GT | | 28 |

TABLE 2-continued

Primer

| Name | Sequences (5' to 3') | Position | SEQ ID NO. |
|---|---|---|---|
| hRIG-I-F | GGA CGT GGC AAA ACA AAT CAG | | 29 |
| hRIG-I-R | GCA ATG TCA ATG CCT TCA | | 30 |
| hTNF-α-F | GGA GAA GGG TGA CCG ACT CA | | 31 |
| hTNF-α-R | CTG CCC AGA CTC GGC AA | | 32 |
| mIFN-β-F | CAC AGC CCT CTC CAT CAA CT | | 33 |
| mIFN-β-R | TCC CAC GTC AAT CTT TCC TC | | 34 |
| m18S-F | CGC GGT TCT ATT TTG GTT T | | 35 |
| m18S-R | TTC GCT CTG GTC CGT CTT G | | 36 |

Figure 7D:
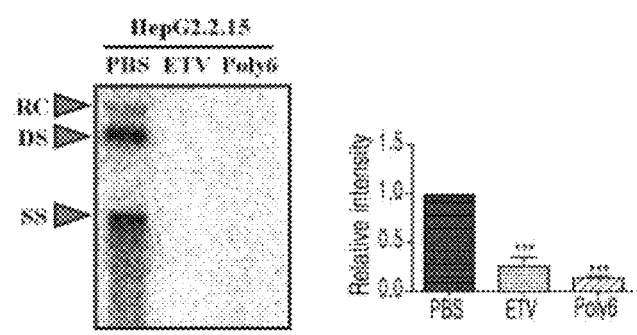
Figure 7E:
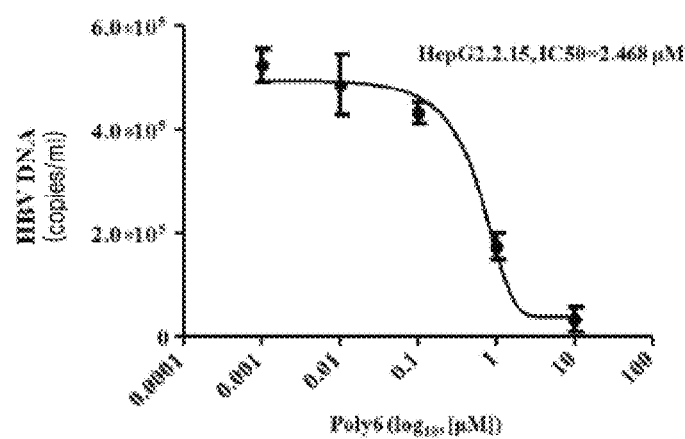

As a result, in the Southern blot analysis, extracellular virion secretion was clearly decreased in Poly6 and ETV, as compared with PBS conditions (FIG. 7D). As a result of examining changes according to the concentration, $IC_{50}$ of HBV by Poly6 was about 2.468 μM (FIG. 7E).

Experimental Example 3. Specific Examination of Mechanism of HBV Inhibition of Poly6

In this Experimental Example, the antiviral mechanism of Poly6 in cells was examined through analysis of nucleocapsid expression, measurement of mitochondrial reactive oxygen species, and experiment of IFN-1.

In detail, as a result of performing Western blot analysis with an anti-HBc antibody (Dako, Agilent Tech), it was confirmed that HBcAg and capsid were significantly reduced in the Poly6-treated group, as compared with the PBS or ETV-treated group. Even when this was quantified using the Image J program, statistical significance was confirmed (FIG. 8A).

It has been revealed that when a reagent is absorbed into a cell and oxidative stress is induced, various reactions including proliferation, cell death, or antiviral effects may be caused by expressing cell factors such as IFN-I. Accordingly, to reveal the mechanism of antiviral effect by oxidative stress-mediated action of Poly6, pHBV-1.2×-wild type transfected HepG2 cells or HepG2.2.15 cells were seeded on a 6-well culture plate at a density of $4 \times 10^5$ cells/well for 24 hours, and treated with PBS, ETV, or Poly6. After culturing the cells for an appropriate time, the cells were incubated with 5 μM of MitoSox (Molecular probes) at 37° C. for 30 min. For flow cytometry, cell pellets were re-suspended in FACS buffer (1% FBS and 1 mM EDTA in PBS) and fixed with 4% paraformaldehyde. To prevent mitochondrial dysfunction, 10 μM of MitoTempo (SigmaAldrich) was pre-treated for 12 hr, and 0.5 μM of rotenone (SigmaAldrich) reagent was used as a positive control for ROS induction through mitochondrial stress.

Figure 10A:
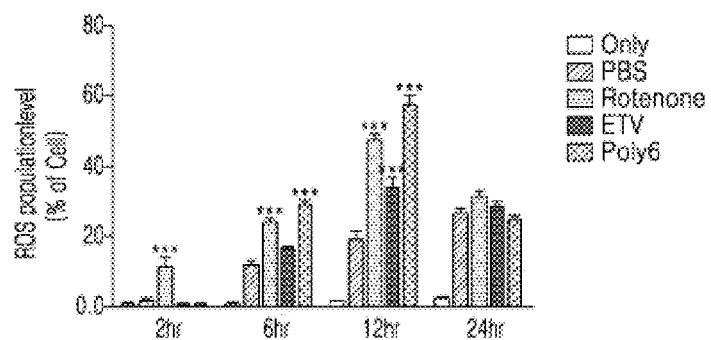
Figure 10B:
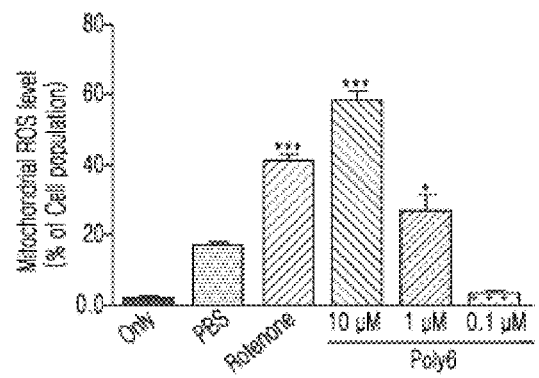
Figure 10C:
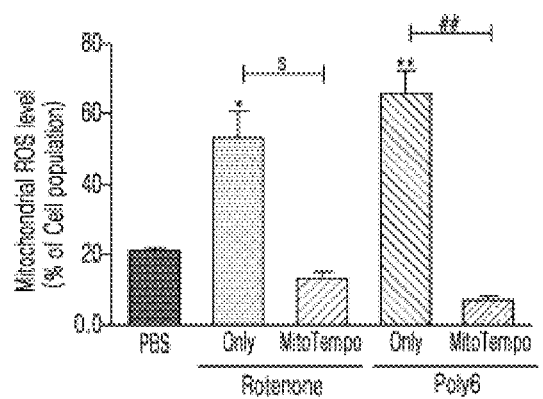

As a result, production of reactive oxygen species (mtROS) by mitochondrial stress in HepG2 cells was significantly increased from 2 hr to 24 hr in the rotenone or Poly6-treated group, as compared with PBS (FIG. 10A). It was confirmed that an increase in mitochondrial reactive oxygen species by Poly6 treatment showed concentration dependence (FIG. 10B). In contrast, the increased pattern of mitochondrial reactive oxygen species was not observed in the entecavir-treated group. The mitochondrial reactive oxygen species increased by treatment with rotenone and Poly6 was reduced again by treatment with MitoTEMPO which is an mtROS-specific antioxidant (FIG. 10C).

IFN-I is induced by host cells to regulate viral infection (Stetson & Medzhitov, 2006). Therefore, to examine the effect of Poly6 on IFN-I production in HepG2-2.15 cells and mouse liver, mRNA levels of IFN-β, RIG-I, and ISG15 were examined.

Figure 11A:
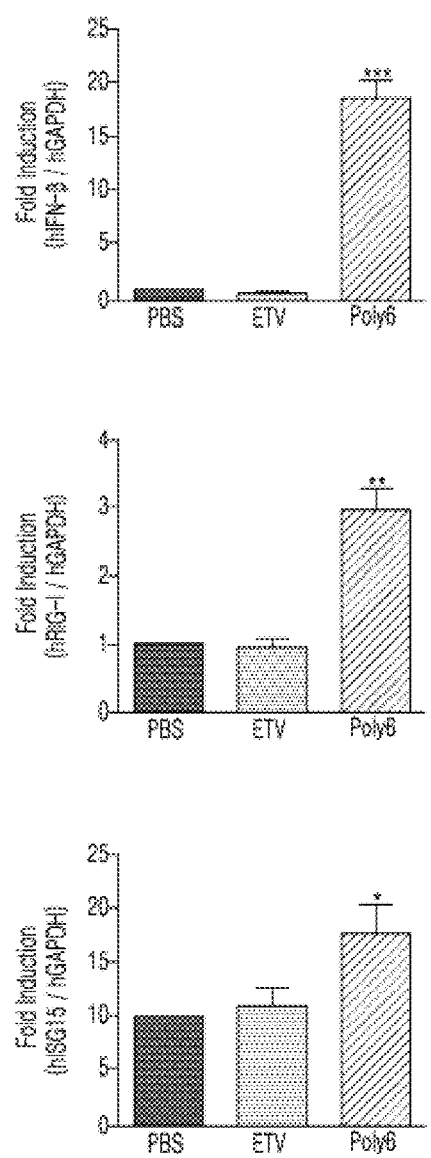
Figure 11B:
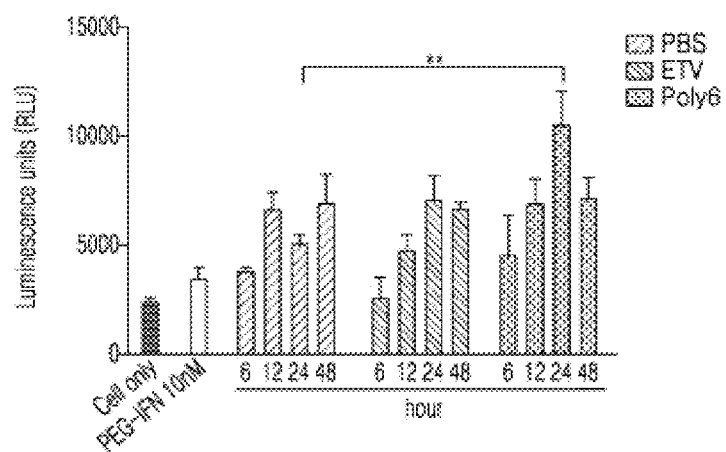
Figure 11C:
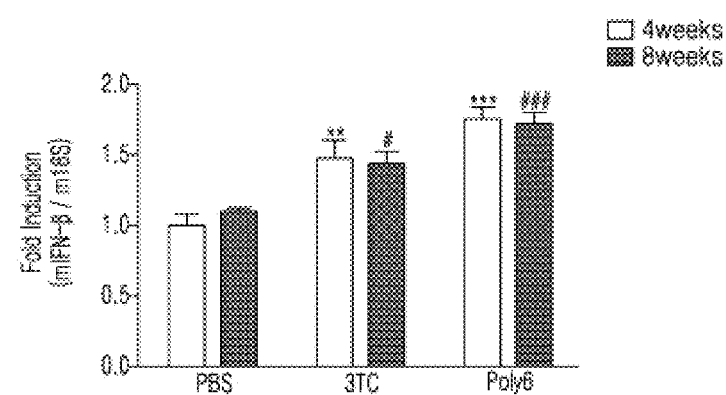
FIG. 11C shows IFN-β mRNA expression levels according to treatment of mouse models with each material.

As a result, it was observed that mRNA levels of IFN-β, RIG-I, and ISG15 were significantly increased in the Poly6-treated group, as compared with the PBS group, and no statistical significance was observed in the entecavir-treated group (FIG. 11A). In addition, to measure IFN levels by indirectly using a luciferase reporter gene for IFN-I bioassay and neutralization analysis, hMH55-293-ISRE cells was used, into which interferon sensitive response element (ISRE) associated with the luciferase reporter gene was inserted at the 3'-end using 5 μg of puromycin (Sigma Aldrich). After collecting supernatants from cells treated with each reagent for 24 hr or 48 hr, the supernatants were added to hMH55-293-ISRE cells for 6 hr. After incubation, cells were washed with PBS, and lysed with a reporter lysis buffer (E1500, Promega) at room temperature for 30 min. A luciferase assay reagent (E1500, Promega) was added and luminescence was measured using a TECAN m200 reader (TECAN). Next day, PBS (0.5%), ETV (30 nM), or Poly6 (10 μM) was added to the cells for 48 hr. As a result, it was confirmed that the luciferase expression level significantly increased at 24 hr according to Poly6 treatment (FIG. 11B).

Figure 12A:
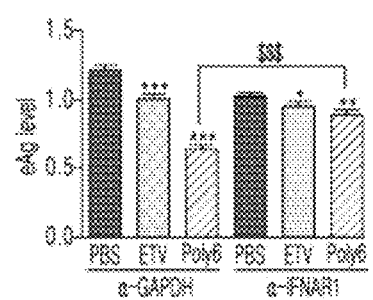
Figure 12A:
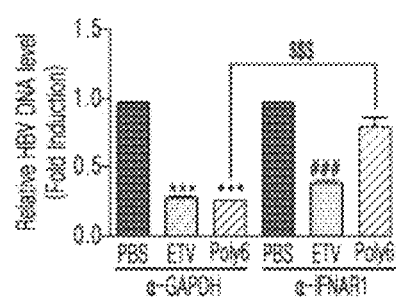
Figure 12B:
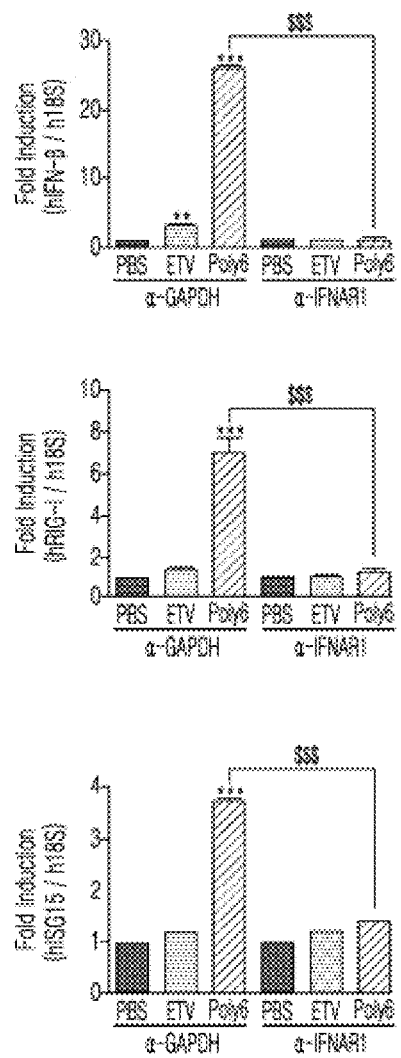

On the other hand, the interaction between interferons and receptors was blocked through a neutralizing type I interferon receptor, and to investigate a change in the anti-HBV effect by Poly6, receptor activation was blocked by treating with a neutralizing antibody at 2 hr before PBS, ETV, or Poly6 treatment, followed by incubation. After incubation for 48 hr after treatment with each material, the anti-HBV effect was evaluated by ELISA and qPCR. As a result, it was confirmed that the HBeAg level reduced by Poly6 in GAPDH antibody treatment significantly increased again by blocking the IFN receptor, and it was confirmed that the HBV DNA level was also recovered to the level of the PBS-treated group (FIG. 12A). Similarly, it was observed that mRNA levels of IFN-β, RIG-I, and ISG15, which were increased by treatment with Poly6, were also reduced by treatment with neutralizing antibodies (FIG. 12B), indicating that Poly6 directly/indirectly affects IFN-I expression.

In conclusion, the above results demonstrated that Poly6 stimulates IFN-β through IFN-I pathway by increasing mitochondrial reactive oxygen species in cells, thereby inhibiting HBV replication while inhibiting HBcAg and protein envelope.

Experimental Example 4. Examination of Anti-Viral Efficacy of Poly6 in In-Vivo System To examine the effect of Poly6 in a mouse model (in vivo), this experimental example was performed. First, to establish a transformed mouse model, transgenic mice expressing mutant HBV W4P were generated in Macrogen, and mice were randomly raised and maintained under the germ-free conditions in Macrogen. The experimental animals were stored in a specific pathogen free laboratory animal center. Briefly, PMSG (7.5 IU) and hCG were intraperitoneally injected into C57BL/6N female mice every 48 hr (5 IU) for 5 weeks to 8 weeks for superovulation. After injection, these female mice were crossed with C57BL/6N male mice. Next day, female mice with vaginal plugs were sacrificed, and fertilized embryos were harvested. The HBV W4P full genome was co-microinjected into one-cell embryo in accordance with standard microinjection procedures for transgenic mouse production (Macrogen). After directly injecting HBV DNA (4 ng/μl) for microinjection into sperm nuclei using a microinjector, the microinjected embryos were incubated at 37° C. for 1 hr to 2 hr. 14 to 16-injected one-cell stage embryos were surgically implanted into the oviduct of pseudopregnant recipient mice (ICR). After F0 was born, genotyping was performed using tail cut samples for the presence of transgenes, and genomic DNA PCR screening through a phenol extraction method was confirmed by PCR analysis.

Then, Poly6 (50 μg/kg) and 3TC (Lamivudine, Sigma-Aldrich, 500 μg/kg) were intravenously administered to a transgenic mouse model expressing HBV virions containing a mutant W4P in the preS1 region (Genotype A, pHY92-W4P) twice a week. HBV DNA and HBsAg levels were measured in mouse sera through orbital sinus blood collection at 4 weeks and 8 weeks.

Figure 9A:
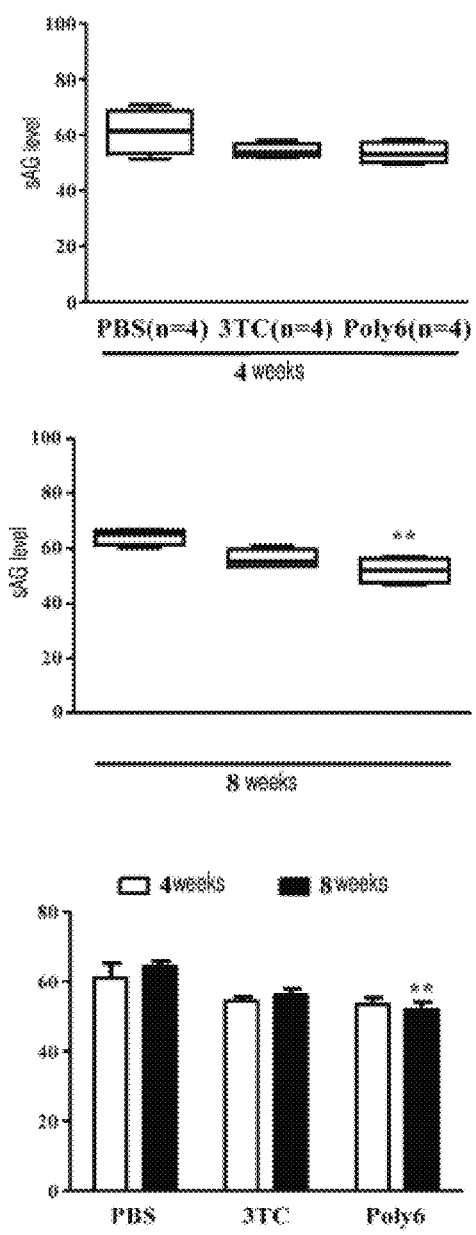
Figure 9B:
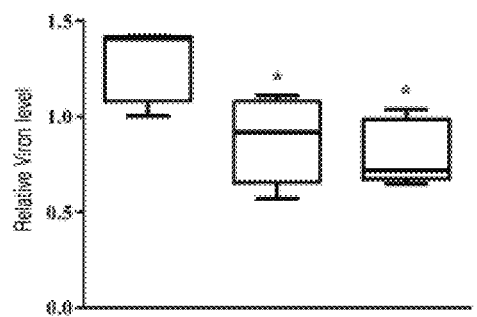
Figure 9B:
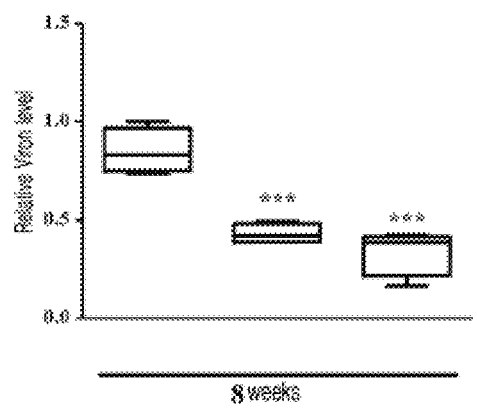
Figure 9B:
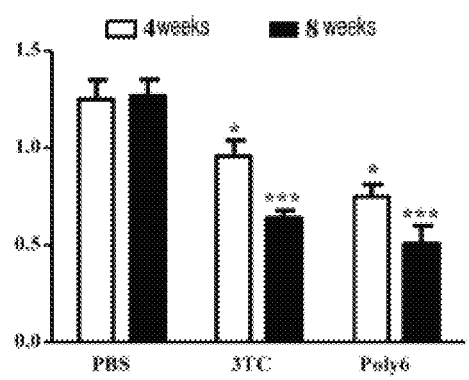

As a result, the HBsAg levels in the sera of mice injected with Poly6 and 3TC were similar to those of mice injected with PBS at 4 weeks, but the HBsAg levels were significantly decreased at 8 weeks in Poly6, as compared with 3TC (FIG. 9A). In addition, HBV DNA levels were decreased about twice in Poly6 and 3TC for 8 weeks, as compared with PBS (FIG. 9B). Finally, IFN-β mRNA level in the liver of the mouse model was assessed. IFN-β mRNA level was significantly increased in the liver tissue at 4 weeks and 8 weeks in the 3TC- or Poly6-treated group, and its higher expression was observed in the poly6-treated group (C of FIG. 11B).

Taken together, these results indicate that Poly6 affects in vivo transgenic mouse model system in which HBsAg and HBV virion levels are decreased.

Experimental Example 5. Synergistic Effect on IFN-1 Increase by Combination Treatment of Poly6 and Entecavir, and Anti-HBV Effect Thereby Through the combination treatment of entecavir, which is currently used as an HBV anti-viral agent having a mechanism whereby activity of HBV polymerase in the nucleus is inhibited and converted to a phosphorylated form, and Poly6, which was confirmed to increase IFN-I, its anti-HBV effect and synergistic effect of IFN-I increase were examined. HepG2-2.15 cells were incubated at a density of 5×10$^5$ cells/well on a 6-well culture plate for 24 hr, and treated with PBS, ETV, or Poly6 alone or in combination of two substances. After incubating the cells for 48 hr, supernatants were collected, and subjected to ELISA, qPCR, and LDH assay.

Figure 13A:
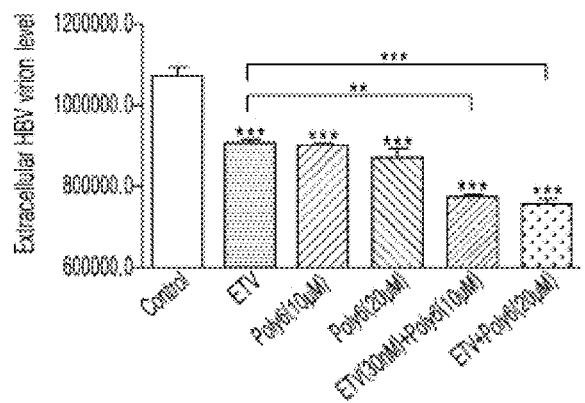
Figure 13B:
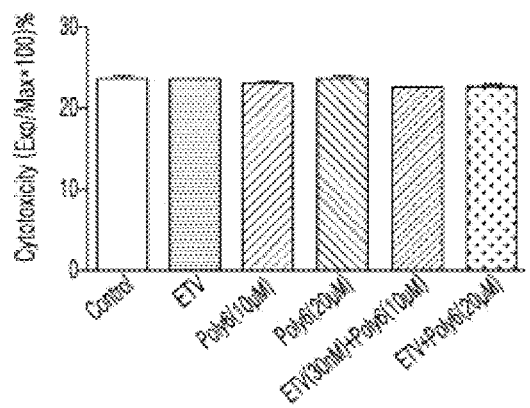
Figure 13C:
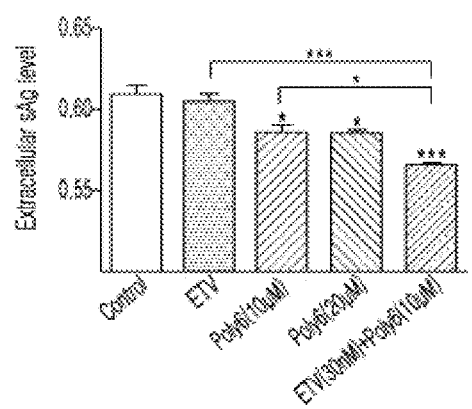
Figure 13C:
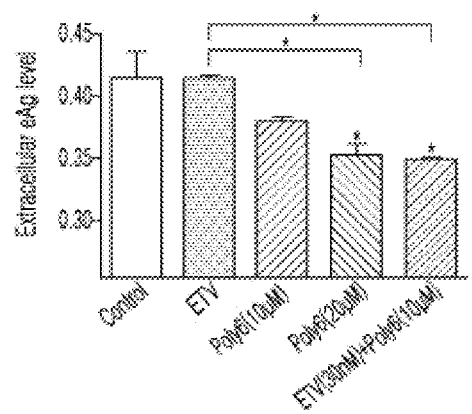

As a result, when ETV or Poly6 alone was treated, the extracellular HBV DNA levels were statistically significantly reduced, as compared with PBS, but the combination treatment of two substances showed more significant reduction effects, and a significant difference was also observed, as compared with single treatment groups (FIG. 13A). As a result of measuring the levels of extracellular s and e antigens, the ETV-treated group showed no significant reduction effect, as compared with the PBS-treated group, but statistical significance was observed in the single Poly6-treated group, and when two substances were used in combination, a significant decrease was observed, as compared with each single treatment group (FIG. 13C).

On the other hand, LDH levels were measured to examine non-specific cytotoxicity levels by single or combination treatment of the substances. No significant difference was observed, as compared with the control group, indicating no cytotoxicity (FIG. 13B).

Figure 14A:
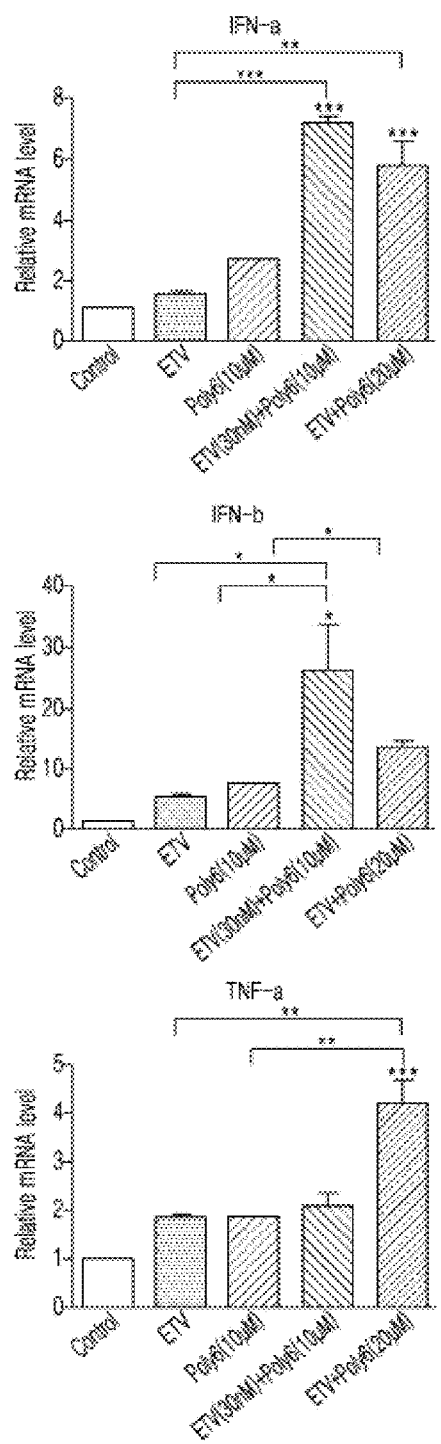
Figure 14B:
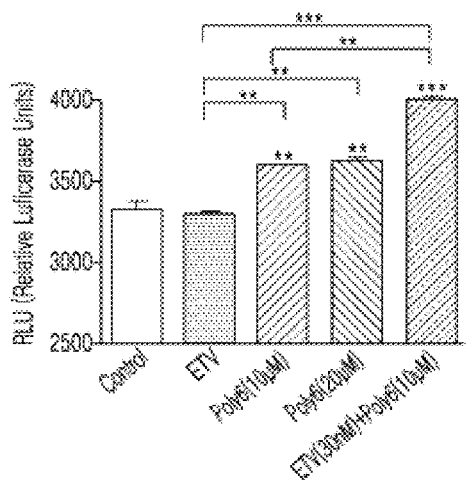

Meanwhile, to examine a synergistic effect of the combination treatment of two substances with respect to the increase level of IFN-I, mRNAs of single treatment groups and combination treatment groups were extracted, and IFN-α, IFN-β, and TNF-α expression levels were observed. As a result, it was confirmed that the mRNA level associated with IFN-1 was significantly increased in the combination treatment groups, as compared with the single treatment groups (FIG. 14A). In addition, IFN levels were indirectly measured using a luciferase reporter gene of hMH55-293-ISRE cell. Consistent with the above results, a statistically significant increase in the luciferase expression levels was observed in the combination treatment group of ETV and Poly6, as compared with PBS treatment group and single treatment groups (FIG. 14B).

The above results demonstrated that the combination treatment of entecavir and Poly6 shows the synergistic effect on IFN-I increase and the anti-viral effect against HBV, and therefore, a synergistic effect on inhibition of liver diseases is expected, when administered in combination.

What is claimed is:

1. An isolated polypeptide comprising an end-capping modification consisting of any one amino acid sequence selected from the group consisting of SEQ ID NO: 1, SEQ ID NO: 2, and SEQ ID NO: 3.

2. The isolated polypeptide of claim 1, wherein the polypeptide consists of the amino acid sequence of SEQ ID NO: 2.

3. The isolated polypeptide of claim 1, wherein the polypeptide has anti-viral activity.

4. The isolated polypeptide of claim 1, wherein the end-capping modification is an N terminus end-capping, a C terminus end-capping, or both.

5. The isolated polypeptide of claim 4, wherein the N terminus end-capping comprises an acetyl and wherein the C terminus end-capping comprises an amide.

6. An anti-viral pharmaceutical composition, comprising the isolated polypeptide of claim 1 and a pharmaceutically-acceptable carrier, excipient or diluent.

7. The anti-viral pharmaceutical composition of claim 6, further comprising an anti-viral agent.

8. The anti-viral pharmaceutical composition of claim 7, wherein the anti-viral agent is selected from the group consisting of acyclovir, famciclovir, valacyclovir, ganciclovir, amprenavir, abacavir, ansamycin, cidofovir, darunavir, delavirdine, efavirenz, etravirine, famciclovir, hypericin, indinavir, lamivudine, lobucavir, nelfinavir, nevirapine, novaferon, ritonavir, saquinavir, stavudine, tipranavir, virazole, ribavirin, zalcitabine, zidovudine, maraviroc, raltegravir, elvitegravir, didanosine, tenofovir, emtricitabine, lopinavir, atazanavir, enfuvirtide, clevudine, entecavir, adefovir, and a combination thereof.

9. The anti-viral pharmaceutical composition of claim 6, wherein the isolated polypeptide suppresses viral replication.

10. The anti-viral pharmaceutical composition of claim 6, wherein the isolated polypeptide inhibits acetylation of human immunodeficiency virus-1 (HIV-1) integrase to inhibit activity of the HIV-1 integrase.

11. The anti-viral pharmaceutical composition of claim 6, wherein the isolated polypeptide increases mitochondrial reactive oxygen species in cells.

12. The anti-viral pharmaceutical composition of claim 6, wherein the isolated polypeptide increases type I interferon (IFN-I) expression.

13. The anti-viral pharmaceutical composition of claim 6, wherein the isolated polypeptide inhibits hepatitis B virus (HBV) hepatitis B core antigen (HBcAg) or nucleocapsid synthesis.

14. A method of restraining, retarding or treating viral infection diseases and symptoms related thereto, the method comprising administering the anti-viral pharmaceutical composition of claim 6 to an individual in need thereof.

15. The method of claim 14, wherein the viral infection diseases are selected from an acquired immune deficiency syndrome (AIDS) caused by viral infection and a liver disease caused by viral infection.

16. The method of claim 15, wherein the AIDS is caused by HIV-1 infection.

17. The method of claim 15, wherein the liver disease is at least one selected from the group consisting of hepatitis, cirrhosis, and liver cancer.

18. The method of claim 14, wherein the viral infection is caused by a virus selected from the group consisting of adenovirus, smallpox virus, polio virus, measles virus, severe fever with thrombocytopenia syndrome virus, influenza virus, hepatitis C virus (HCV), human immunodeficiency virus-1 (HIV-1), and hepatitis B virus (HBV).

19. The method of claim 15, wherein the liver disease is caused by infection with HBV.

* * * * *